(12) United States Patent
Minne et al.

(10) Patent No.: US 12,376,915 B2
(45) Date of Patent: Aug. 5, 2025

(54) AUTOMATED TOUCHLESS REGISTRATION FOR SURGICAL NAVIGATION

(71) Applicant: Digital Surgery Systems, Inc., Goleta, CA (US)

(72) Inventors: Stephen C. Minne, Goleta, CA (US); George C. Polchin, Goleta, CA (US); Alan Fridman, Goleta, CA (US); Michael Larkin, Goleta, CA (US)

(73) Assignee: Digital Surgery Systems, Inc., Goleta, CA (US)

( * ) Notice: Subject to any disclaimer, the term of this patent is extended or adjusted under 35 U.S.C. 154(b) by 0 days.

(21) Appl. No.: 18/281,429

(22) PCT Filed: Mar. 11, 2022

(86) PCT No.: PCT/US2022/019979
§ 371 (c)(1),
(2) Date: Sep. 11, 2023

(87) PCT Pub. No.: WO2022/192690
PCT Pub. Date: Sep. 15, 2022

(65) Prior Publication Data
US 2024/0299100 A1    Sep. 12, 2024

Related U.S. Application Data

(60) Provisional application No. 63/160,100, filed on Mar. 12, 2021.

(51) Int. Cl.
*A61B 34/20* (2016.01)
*A61B 34/10* (2016.01)
(Continued)

(52) U.S. Cl.
CPC .............. *A61B 34/20* (2016.02); *A61B 34/10* (2016.02); *A61B 34/32* (2016.02); *G06T 7/0014* (2013.01);
(Continued)

(58) Field of Classification Search
CPC ... A61B 34/20; A61B 90/50; A61B 2090/371; A61B 2560/0437; A61B 90/14;
(Continued)

(56) References Cited

U.S. PATENT DOCUMENTS

2002/0077543 A1    6/2002   Grzeszczuk et al.

FOREIGN PATENT DOCUMENTS

WO    2019/195926 A1    10/2019

OTHER PUBLICATIONS

Wengert Christian et al. "Markerless Endoscopic Registration and Referencing," Oct. 1, 2006, Advances in Biometrics, International Conference, ICB 2007, Seoul, Korea, pp. 816-823, XP047461456, ISBN: 978-3-540-74549-5 (Year: 2006).*

(Continued)

*Primary Examiner* — Sath V Perungavoor
*Assistant Examiner* — Tyler B Edwards
(74) *Attorney, Agent, or Firm* — K&L Gates LLP; Dennis A. Majewski

(57) ABSTRACT

Systems and methods are disclosed for an automated touchless registration of patient anatomy for surgical navigation systems. An example method includes: acquiring a plurality of images of the patient; determining relevant objects from a plurality of poses; and processing the received images through a photogrammetry module. The photogrammetry module may provide camera calibration and facilitate camera registration. As such, manual movement or robotic movement capabilities of the camera head, and digital visualization capabilities of a digital surgical microscope (Continued)

disclosed herein can be extended to allow near-automated or fully automated touchless registration for traditional surgical navigation.

20 Claims, 25 Drawing Sheets

(51) Int. Cl.
*A61B 34/32* (2016.01)
*G06T 7/00* (2017.01)
*G06T 7/73* (2017.01)
*G06T 7/80* (2017.01)
*G06T 11/00* (2006.01)
*H04N 13/246* (2018.01)

(52) U.S. Cl.
CPC .................. *G06T 7/75* (2017.01); *G06T 7/85* (2017.01); *G06T 11/00* (2013.01); *H04N 13/246* (2018.05); *A61B 2034/105* (2016.02); *A61B 2034/2057* (2016.02); *G06T 2207/10012* (2013.01); *G06T 2207/30004* (2013.01); *G06T 2210/41* (2013.01)

(58) Field of Classification Search
CPC .. A61B 2017/00725; A61B 2034/2065; A61B 2090/365; A61B 90/20; A61B 90/25; A61B 2034/2055; A61B 2090/3983; A61B 34/10; A61B 2034/2057; A61B 2017/00203; A61B 2017/00207; A61B 2017/00216; A61B 2034/105; A61B 34/32; G06T 2207/10012; G06T 2207/30004; G06T 2210/41; G06T 11/00; G06T 7/85; G06T 7/75; G06T 7/0014; H04N 13/246

See application file for complete search history.

(56) References Cited

OTHER PUBLICATIONS

Wengert et al., "Markerless Endoscopic Registration and Referencing", Advances in Biometrics: International Conference, ICB 2007, Seoul, Korea, Dated Oct. 1, 2006, pp. 816-823.
International Search Report and Written Opinion of PCT/US2022/019979, Dated Jun. 24, 2022, in 87 pages.

* cited by examiner

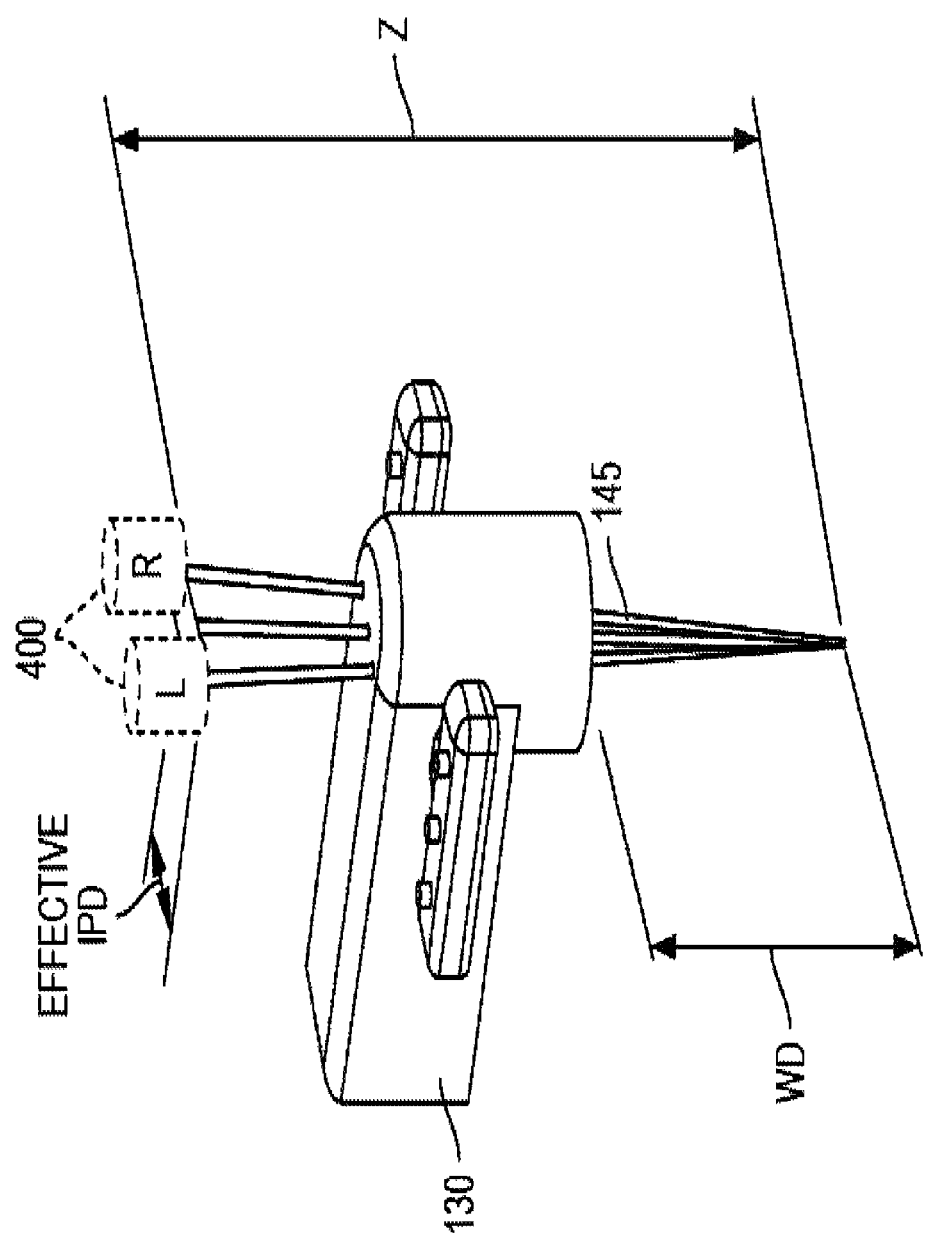

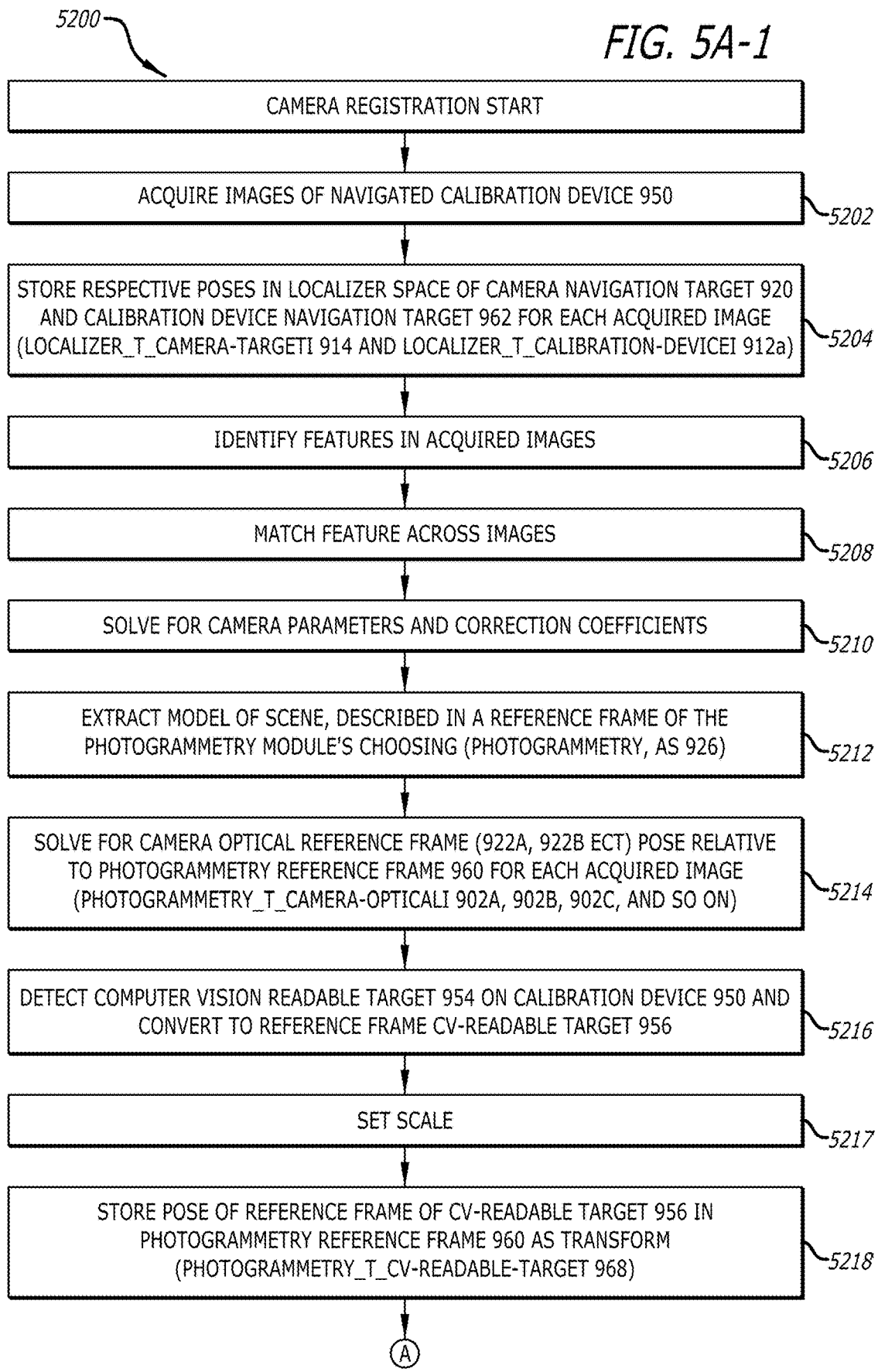

┌─────────────────────────────────────────────────────────────┐
│ CALCULATE TRANSFORM (OR KNOW BY DESIGN OR FIND BY MEASUREMENT) BETWEEN │
│ REFERENCE FRAME OF CV-READABLE TARGET 956 AND CALIBRATION DEVICE │
│ NAVIGATION TARGET 964 (CALIBRATION-DEVICE-_T_CV-READABLE-TARGET 966) │ — 5220
└─────────────────────────────────────────────────────────────┘
                                ↓
┌─────────────────────────────────────────────────────────────┐
│ USING AFOREMENTIONED TRANSFORMS CALCULATE CAMERA OPTICAL REFERENCE │
│ FRAME (922A, 922B ETC) POSE RELATIVE TO CALIBRATION DEVICE NAVIGATION │
│ TARGET 964 FOR EACH ACQUIRED IMAGE: │
│ CALIBRATION-DEVICE_T_CAMERA-OPTICALI * │
│ CALIBRATION-DEVICE_T_CV-READABLE-TARGET * │
│ CV-READABLE-TARGET_T_PHOTOGRAMMETRY* │
│ PHOTOGRAMMETRY_T_CAMERA-OPTICALI │
│ │
│ WHERE FOR CLARITY │
│ CALIBRATION-DEVICE_T-CAMERA-OPTICALI IS NOT LABELED, │ — 5222
│ CALIBRATION-DEVICE_T_CV-READABLE-TARGET IS 966, │
│ CV-READABLE-TARGET_T_PHOTOGRAMMETRY IS 968 INVERSE, AND │
│ PHOTOGRAMMETRY_T_CAMERA-OPTICALI IS 902A, 902B, 902C AND SO ON │
└─────────────────────────────────────────────────────────────┘
                                ↓
┌─────────────────────────────────────────────────────────────┐
│ USING STORED RESPECTIVE POSES (914A, 914B, ETC, AND 912A, 912B, ETC) IN │
│ LOCALIZER SPACE OF CAMERA NAVIGATION TARGET (920A, 920B ETC) AND │
│ CALIBRATION DEVICE NAVIGATION TARGET 964 CALCULATE RESPECTIVE CAMERA │
│ OPTICAL REFERENCE FRAME (922A, 922B, ETC) POSE RELATIVE TO CAMERA │
│ NAVIGATION TARGET (920A, 920B, ETC) FOR EACH ACQUIRED IMAGE: │
│ CAMERA-TRAGET_T_CAMERA-OPTICALI = │
│ CAMERA-TARGET_T_LOCALIZERI * │
│ LOCALIZER _T_CALIBRATION-DEVICEI * │
│ CALIBRATION-DEVICE_T_CAMERA-OPTICALI │
│ WHERE │ — 5224
│ CAMERA-TARGET_T_CAMERA-OPTICALI IS 900, │
│ CAMERA-TARGET_T_LOCALIZERI = │
│ LOCALIZER_T_CAMERA-TARGETI.INVERSE() (914 INVERSE), │
│ LOCALIZER_T_CALIBRATION-DEVICEI IS 912A, AND │
│ CALIBRATION-DEVICE_T_CAMERA-OPTICALI │
│ IS A CALCULATED IN PRIOR STEP AND FOR CLARITY IS NOT LABELED │
└─────────────────────────────────────────────────────────────┘
                                ↓
┌─────────────────────────────────────────────────────────────┐
│ DETERMINE A SINGLE CAMERA OPTICAL REFERENCE FRAME POSE RELATIVE TO │
│ CAMERA NAVIGATION TARGET (CAMERA-TARGET_T_CAMERA-OPTICAL 900) BY │ — 5226
│ AVERAGING THE RESULTS OF THE SAME FOR ALL ACQUIRED IMAGES │
└─────────────────────────────────────────────────────────────┘

CALCULATE
PATIENT-TARGET_T_PATIENT-DATAI
=
PATIENT-TARGET_T_LOCALIZERI *
LOCALIZER_T_CAMERA-TARGETI *
CAMERA-TARGET_T_CAMERA-OPTICAL *
CAMERA-OPTICAL_T_PHOTOGRAMMETRY *
PHOTOGRAMMETRY_T_PATIENT-DATA

FOR EACH OF THE RESPECTIVE POSES STORED AT WITH THE ACQUIRED IMAGES
WHERE

PATIENT-TARGET_T_PATIENT-DATAI IS 970,
PATIENT-TARGET_T_LOCALIZERI = LOCALIZER_T_PATIENT-
TARGETI.INVERSE() (912 INVERSE),
LOCALIZER_T_CAMERA-TARGETI IS 914,
CAMERA-TARGET_T_CAMERA-OPTICAL IS 900
CAMERA-OPTICAL_T_PHOTOGRAMMETRY =
PHTOTGRAMMETRY_T_CAMERA-OPTICAL.INVERSE() (902 INVERSE),
PHOTOGRAMMETRY_T_PATIENT-DATA IS 946 AND
CAMERA-TARGET_T_CAMERA-OPTICAL 900
IS AS CALCULATED IN PRIOR STEP

5320

DETERMINE A SINGLE
PATIENT-TARGET_T_PATIENT-DATA 970
BY AVERAGING THE RESULTS OF SAME FOR ALL ACQUIRED IMAGES

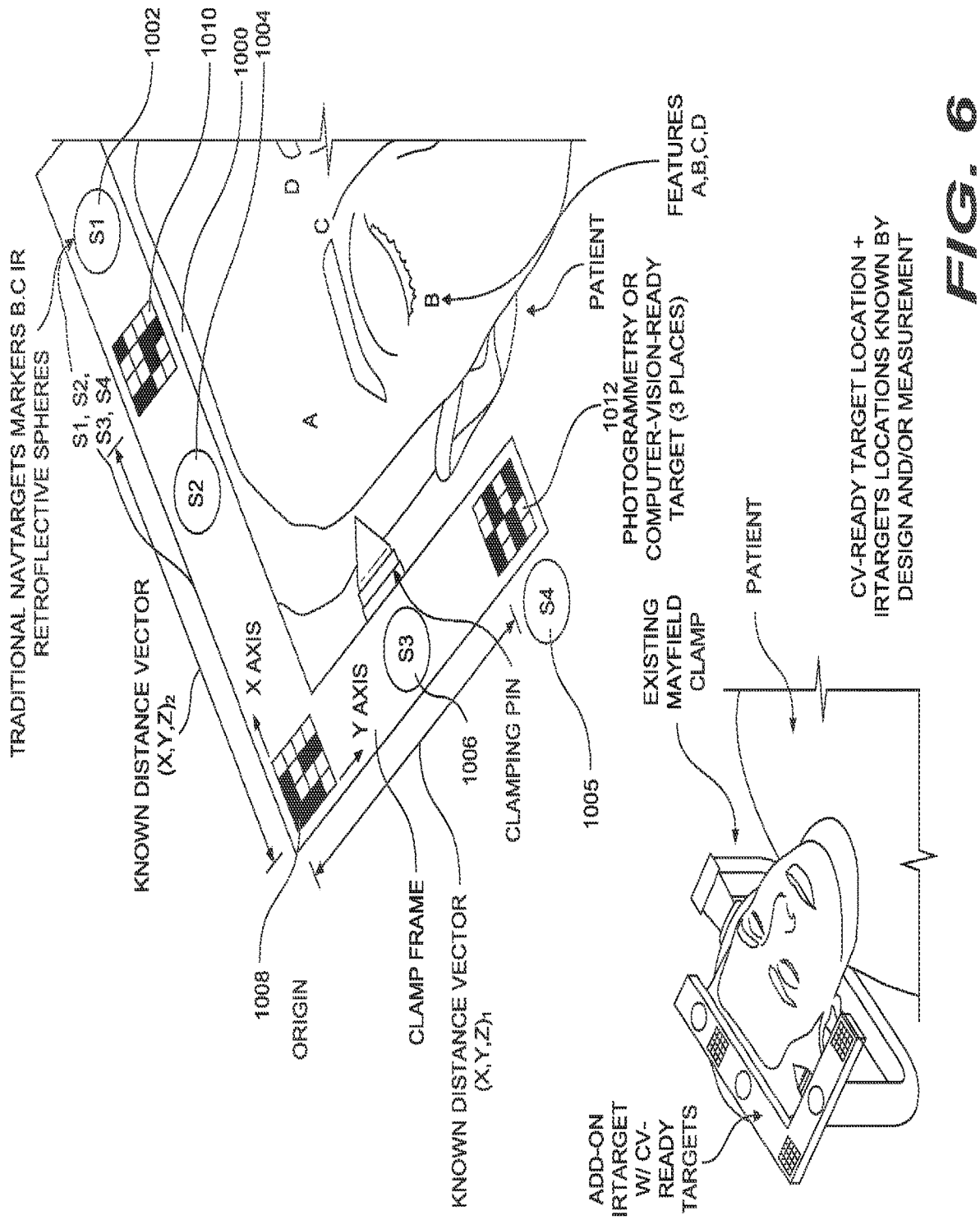

AUTOMATED TOUCHLESS REGISTRATION FOR SURGICAL NAVIGATION

PRIORITY CLAIM

The present application is a national phase entry of PCT Patent Application No. PCT/US2022/019979, filed on Mar. 11, 2022, which claims priority to and the benefit of U.S. Provisional Patent Application No. 63/160,100, filed on Mar. 12, 2021, the entirety of which is are incorporated herein by reference.

TECHNICAL FIELD

The present application relates to stereoscopic surgical systems, and more specifically to touchless registration of patient anatomy for surgical navigation systems.

BACKGROUND

Surgical navigation provides information to a user indicative of "where am I" in a patient's 3D anatomy. This enables showing the location, relative to a patient, of a tool feature such as a probe tip or a microscope focal point by displaying a representation of the feature within a separate representation of a 3D patient scan such as a computerized tomography (CT) or magnetic resonance imaging (MRI) scan. To do this, surgical navigation requires a means to track the pose of the patient anatomy of interest, a means to track the pose of the tool in the same reference frame as the patient anatomy, and a means to register the live patient anatomy with the pre-existing 3D scan data such as CT or MRI images.

Applications such as augmented reality overlay patient data onto a live view and have a further requirement of knowing the pose of the camera optical system relative to the patient anatomy (as opposed to just the location of the focal point). This is enabled in part by determining, through a camera registration process, the pose of the camera optical system relative to the navigation target mounted on the camera. Additionally, for augmented reality, an optical model of the camera system must be found through a camera calibration process.

The typical current state of the art mounts patient anatomy in a clamp, such as mounting a patient's cranium in a Mayfield clamp for cranial surgery. A trackable target such as a unique geometrical array of retroreflective spheres or a 2D or 3D set of trackable two-dimensional patterns are mounted to the clamp, which is also called the patient frame. A tracking camera (known as the localizer) views the scene including the probe and the patient frame target. The localizer reports pose information for each tool it discerns within its view, up to a limit of a small number of tools.

A navigation camera-trackable target is secured rigidly relative to the camera of the digital surgical microscope. A registration routine finds the pose of the camera optical system in the target's reference frame. Design processes are used alternatively or in conjunction with registration to find said pose.

With knowledge of the pose of the camera optical system relative to the camera target, as well as the pose of the camera target relative to the localizer, plus the pose of the patient frame target relative to the localizer, the patient anatomy pose relative to the patient frame target is a missing piece to enable location of the camera optical system relative to the patient anatomy and is found via a process called patient registration.

The current state of the art locates points or surface features on the patient via several means including a navigated probe, a projected laser point, and flexible structures that lie on the patient anatomy surface. Furthermore, the current state of the art relies on discrete or individually paired systems (e.g., a surgical navigation system and a surgical visualization system), which can lead to difficulties in setup and use.

Various embodiments of the present disclosure overcome one or more of these shortcomings.

SUMMARY

In this disclosure, the above-known methods are replaced with a touchless process based on acquiring a plurality of images of the patient and other relevant objects from many poses and processing the images through a photogrammetry module. In a further embodiment, the photogrammetry module also enables the camera calibration and camera registration processes. As such, manual movement or robotic movement capabilities of the camera head, and digital visualization capabilities of a digital surgical microscope disclosed herein are extended to enable near-automated or fully automated touchless registration for traditional surgical navigation. This is a more accurate, faster, and more automated procedure than existing methods. A further embodiment uses a camera that has already been calibrated; that is, the camera calibration is separated from the act of extracting patient features.

In an example, a surgical navigation system for patient registration is disclosed. The system may include a moveable arm and a visualization camera connected to the moveable arm The visualization camera includes at least one navigation camera trackable target mounted to a housing of the visualization camera. The system also includes a navigation camera (e.g., a localizer), and a computer system communicatively coupled to the visualization camera and the navigation camera. The computer system may be configured to receive images of patient anatomy and solve for one or more camera parameters and one or more correction coefficients. For each received image, the computer system may be configured to store, in a localizer space, a pose of the navigation camera trackable target and a patient target, respectively as Localizer_T_Camera-Target$_i$ transform and Patient-Target_T_Localizer$_i$ transform, extract a model of a patient anatomy described in a photogrammetry reference frame using a photogrammetry module, and solve for a camera optical reference frame pose relative to a photogrammetry reference frame to store as Photogrammetry_T_Camera-Optical$_i$ transform. The computer system may also be configured to detect a target within the received image and use said target to a set scale, match the extracted model of the patient anatomy with the patient anatomy representation in patient data to obtain a Photogrammetry_T_Patient Data transform, and calculate, for each of the respective poses associated with the received image, a Patient-Target_T_Patient_Data$_i$ transform using the Patient-Target_T_Localizer$_i$ transform, the Localizer_T_Camera-Target$_i$ transform, a Camera-Target_T_Camera-Optical transform, the Photogrammetry_T_Camera-Optical$_i$ transform, and the Photogrammetry_T_Patient Data transform. The computing system may further be configured to average some or all of the Patient-Target_T_Patient_data$_i$ transforms of each of the respective poses associated with each of the received images to determine a single Patient-Target_T_Patient_Data transformation, and display, using the Patient-Target_T_

Patient_Data, the patient data overlaid on live surgical images recorded by the visualization camera.

In another example, a system for determining a pose of a camera optical reference frame relative to a camera navigation target (e.g., Camera-Target_T_Camera-Optical transform) is disclosed. The system may include a processor and memory. The memory may store instructions that, when executed by the processor, cause the processor to receive, via a visualization camera, images of a navigated calibration device and solve for camera parameters and correction coefficients. For each received image, the instructions may cause the processor to store, in a localizer space, a pose of the camera navigation target and a calibration device navigation target, respectively as a Localizer_T_Camera-Target$_i$ transform and a Localizer_T_Calibration-Device$_i$ transform, extract a model of a scene provided in a reference frame as selected by a photogrammetry module, solve for a camera optical reference frame pose relative to a photogrammetry reference frame to store as Photogrammetry_T_Camera-Optical$_i$ transform, detect a computer vision readable target on the navigated calibration device and convert to a reference frame, use the computer vision readable target to set a scale; store a pose of the reference frame of the computer vision readable target in the photogrammetry reference frame as a Photogrammetry_T_CV-Readable-Target transform, calculate a Calibration-Device_T_CV-Readable-Target transform between the reference frame of the computer vision readable target and the calibration device navigation target, generate, using the Calibration-Device_T_CV-Readable-Target transform, the Photogrammetry_T_CV-Readable-Target, and the Camera-Optical$_i$_T_Photogrammetry transform, a camera optical reference frame pose relative to the calibration device navigation target as a Calibration-Device_T_Camera-Optical$_i$ transform, and generate, using the stored poses in the localizer space of the camera navigation target and the calibration device navigation target, respective camera optical reference frame poses relative to the camera navigation target such that a Camera-Target_T_Camera-Optical$_i$ transform is equal to a combination of the Localizer_T_Camera-Target$_i$ transform, the Localizer_T_Calibration-Device$_i$ transform, and the Calibration-Device_T_Camera-Optical$_i$ transform. Furthermore, the instructions may cause the processor to determine, as the Camera-Target_T_Camera-Optical transform, a single camera optical reference frame pose relative to the camera navigation target by averaging the results of the same for all received images.

In another example, a method for patient registration in a surgical navigation system is disclosed. The method may include receiving, by a computer system communicatively coupled to the visualization camera and the navigation camera, images of patient anatomy, and solving for one or more camera parameters and one or more correction coefficients. For each received image, the computing device may store, in a localizer space, a pose of the navigation camera trackable target and a patient target, respectively as Localizer_T_Camera-Target$_i$ transform and Patient-Target_T_Localizer$_i$ transform; extract a model of a patient anatomy described in a photogrammetry reference frame using a photogrammetry module; solve for a camera optical reference frame pose relative to a photogrammetry reference frame to store as Photogrammetry_T_Camera-Optical$_i$ transform; detect a target within the received image and use said target to a set scale; match the extracted model of the patient anatomy with the patient anatomy representation in patient data to obtain a Photogrammetry_T_Patient Data transform; and calculate, for each of the respective poses associated with the received image, a Patient-Target_T_Patient_Data$_i$ transform using the Patient-Target_T_Localizer$_i$ transform, the Localizer_T_Camera-Target$_i$ transform, a Camera-Target_T_Camera-Optical transform, the Photogrammetry_T_Camera-Optical$_i$ transform, and the Photogrammetry_T_Patient Data transform. The method may further include: averaging some or all of the Patient-Target_T_Patient_data$_i$ transforms of each of the respective poses associated with each of the received images to determine a single Patient-Target_T_Patient_Data transformation; and displaying, using the Patient-Target_T_Patient_Data, the patient data overlaid on live surgical images recorded by the visualization camera.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIG. 4 illustrates a diagram of a calibrated stereoscopic camera in which the optical intrinsic and/or extrinsic parameters are fully characterized, according to an example embodiment of the present disclosure.

FIG. 5A illustrates an example procedure or routine for determining a patient registration and incidentally a camera calibration and a camera registration for the stereoscopic navigation systems of FIG. 1, according to an example embodiment of the present disclosure.

FIG. 6 is a diagram of a surgical navigation target with computer-vision ("CV")-ready targets, according to an example embodiment of the present disclosure.

DETAILED DESCRIPTION

Figure 1:
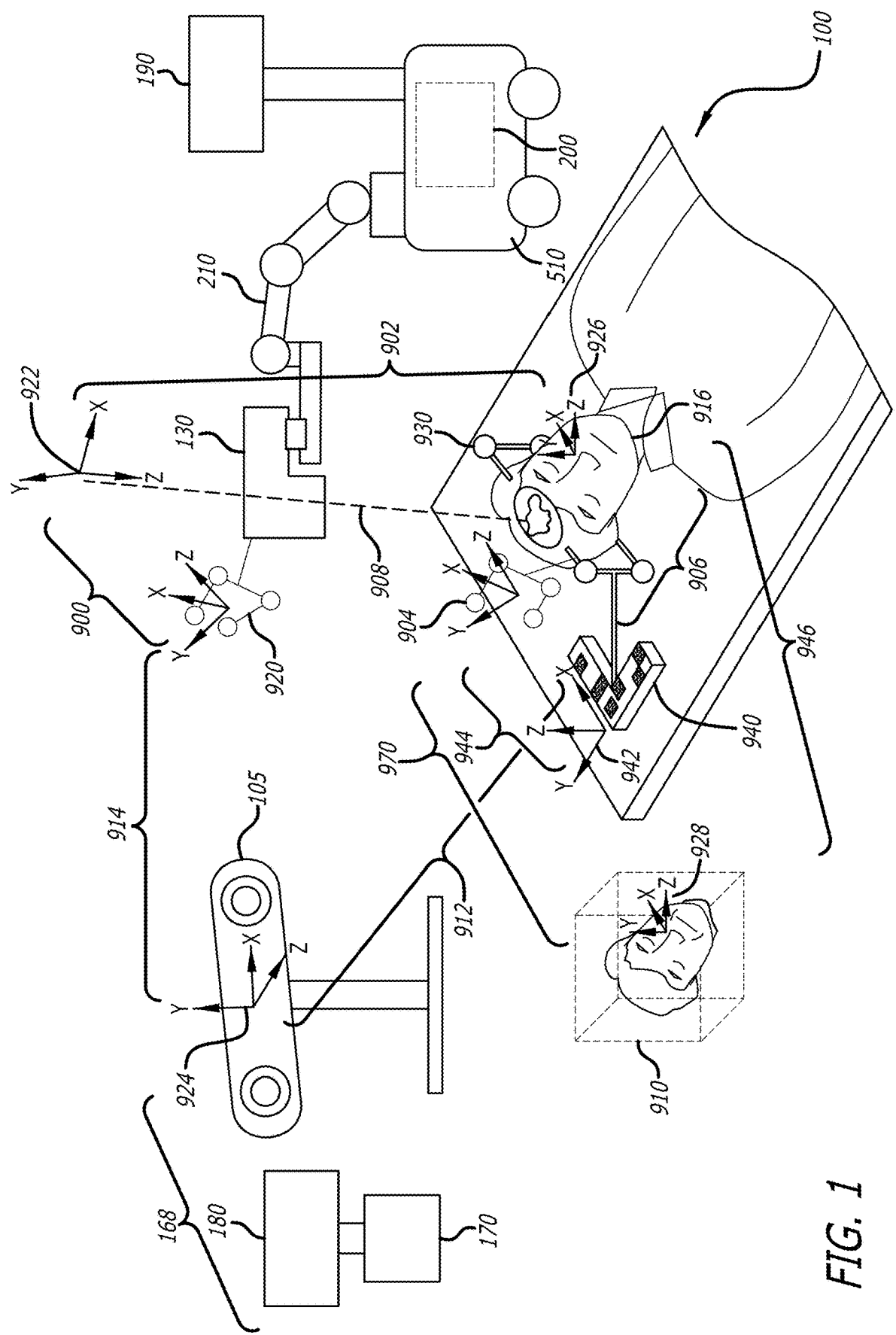
FIG. 1 shows a diagram of a surgical navigation system with a localizer, set up for patient registration and incidentally camera calibration and camera registration, and finally augmented reality based surgical navigation, according to an example embodiment of the present disclosure.

The task of patient registration, as disclosed herein, is to position and orient patient scan data such as CT and MRI data in a patient frame in the same way that the live patient is positioned and oriented. This is implemented in practice by finding features in both the live patient anatomy and in the patient scan data and aligning the features using a measurable transformation. For example, the inner and outer corners of the eyes as well as a corner of the nose can be located in each dataset and aligned manually by a user or automatically by an algorithm in software disclosed herein.

The features used in alignment must be readily accessible in both the live situation and in the scan data. For scans that happen relatively close in time to a surgical procedure, mechanical or other types of fiducials are added to the live patient, for example by affixing a mechanical shape that is visible on the live patient as well as in the scan data. To enable unique alignment, the shape may have features such as asymmetry or else multiple such shapes are added in an asymmetric pattern.

For a more general solution that does not necessarily rely on added fiducials, surface features of the patient anatomy are typically used. For example, the software disclosed herein prompts a user to place the tip of the navigated probe on a feature shown on the patient data, for example, the outer corner of the patient's left eye. Such features are optionally selected manually in the patient data by the user prior to use of the system, or are selected automatically using a previously programmed algorithm. Additionally, the shape of a surface is considered a feature such that the user is optionally prompted to trace the probe over and about the saddle of the nose and eye sockets.

Once a set of matching shapes/features is found in both the patient scan data and the live patient, registration is achieved by solving for a transformation that moves one set to align with the other set with a minimum of error based on some heuristic. Iterative closest point is one method of achieving this. Another (for example aligning four points with each other) is to "find the optimal transformation" using centroid matching and singular value decomposition, or "find the homography" between the two sets. The disclosed system may use any alignment method for performing the registration provided herein.

The disclosed system provides an automated touchless means of extracting locations of surface features from a live patient in a certain reference frame, called here the "photogrammetry" frame.

The disclosed system also provides a means of registering the photogrammetry frame to a navigation frame (also called a "patient target reference frame"), which patient target reference frame is trackable by a surgical navigation system tracking camera such as an NDI Polaris Vega™ localizer camera. It is understood that the disclosed system is adaptable to use any existing surgical navigation systems.

Referring to the drawings, a camera calibration and calibration registration process is first described. A calibrated and registered camera is in general required in the touchless registration process, and while the calibration information can be obtained via other methods, the camera calibration and registration process using the photogrammetry module is nearly identical to the patient registration method. In fact, one embodiment enables simultaneous camera calibration, camera registration, and patient registration.

Various embodiments of the present disclosure also describe an integrated surgical visualization and navigation system that is configured to perform the patient registration methods described herein. The use of a single integrated system (e.g., a single medical device) helps to reduce operating room (OR) footprint. This reduction is important in most operating rooms, which are already crowded due to the many medical devices required for most surgeries.

Surgical Navigation Embodiments

Figure 2:
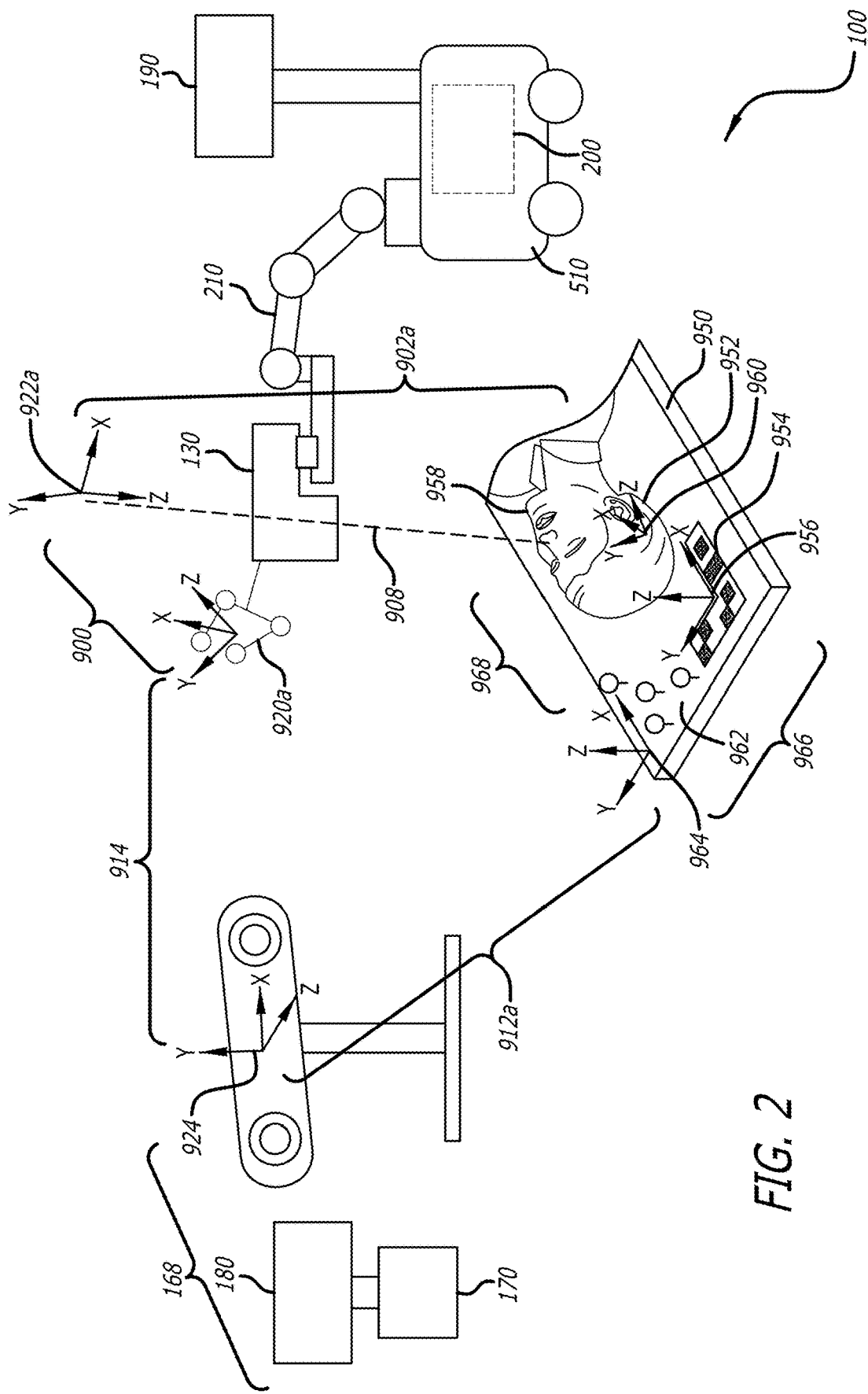
FIG. 2 shows a diagram of a calibration and registration setup, according to an example embodiment of the present disclosure.
Figure 3:
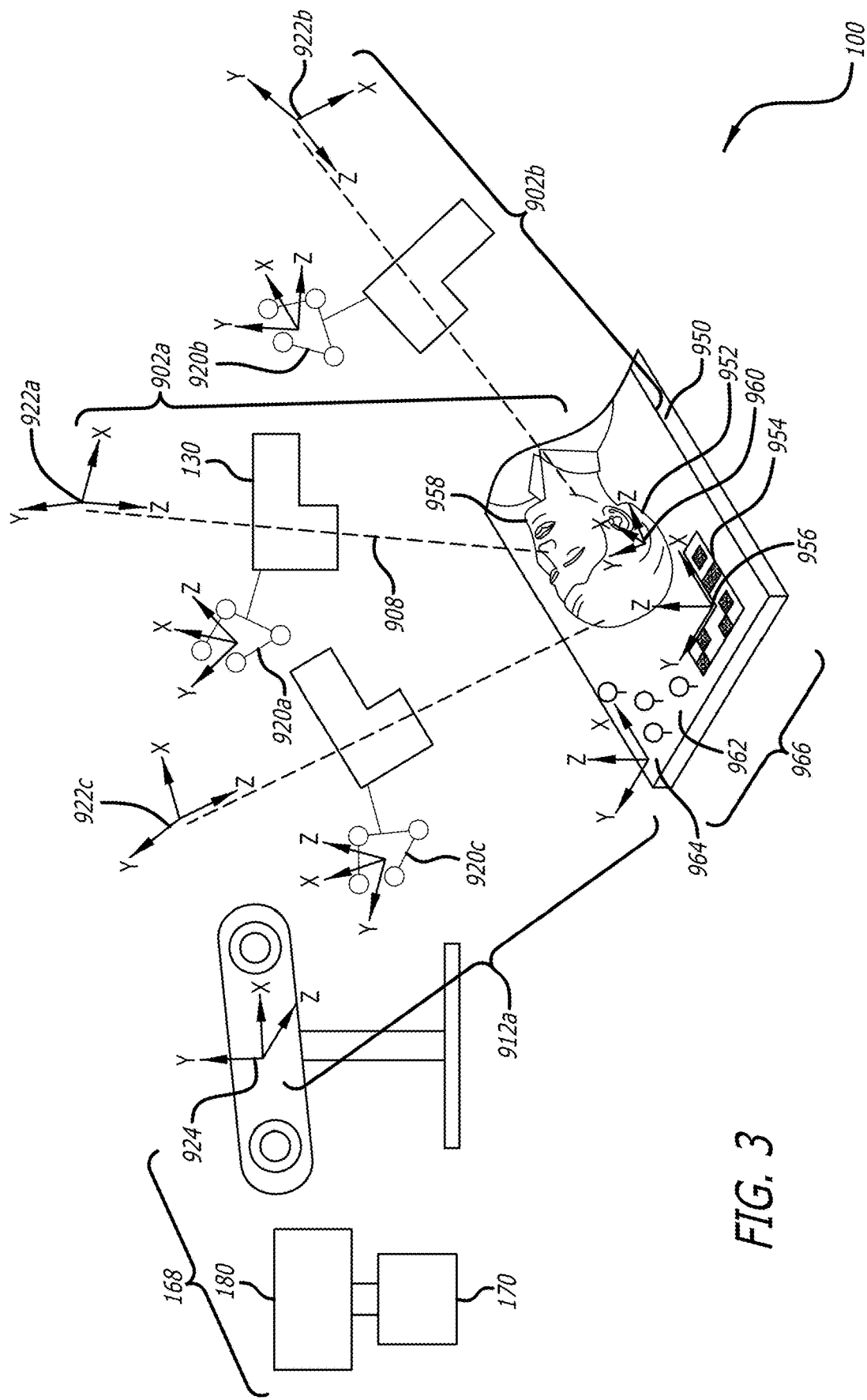
FIG. 3 is a diagram of the plurality of poses taken during the various patient registration, camera calibration and camera registration processes according to an example embodiment of the present disclosure.

FIGS. 1 to 3 show diagrams of a surgical navigation system 100, according to an example embodiment of the present disclosure. FIG. 1 shows the surgical navigation system 100 with a localizer, set up for patient registration and incidentally camera calibration and camera registration, and finally augmented reality based surgical navigation. FIG. 2 shows a diagram of a calibration and registration setup, according to an example embodiment of the present disclosure. FIG. 3 is a diagram of the plurality of poses taken during the various patient registration, camera calibration and camera registration processes according to an example embodiment of the present disclosure.

The system 100 of FIGS. 1 to 3 includes a navigation camera 105 (e.g., a localizer), a digital surgical microscope head 130, a navigation system 168, a navigation computer system 170, a navigation computer display 180, a digital surgical microscope display 190, a digital surgical microscope computer system 200, a digital surgical microscope robotic arm 210, a digital surgical microscope cart 510, a CAMERA-TARGET_T_CAMERA-OPTICAL$_i$ transformation 900, a PHOTOGRAMMETRY_T_CAMERA-OPTICALi (viewing patient anatomy during registration and during runtime) transformation 902, a PHOTOGRAMMETRY_T_CAMERA-OPTICAL$_i$ transformation 902a, 902b, and 902c during camera calibration (a plurality of poses), a patient target reference frame 904 (e.g., a target on clamp and associated reference frame—PATIENT TARGET), a PATIENT-TARGET_T_PHOTOGRAMMETRY transformation 906, and optical axis 908, patient volume data 910, a LOCALIZER_T_PATIENT-TARGET transformation 912, a LOCALIZER_T_CALIBRATION-DEVICE transformation 912a, a LOCALIZER_T_CAMERA-TARGET transformation 914, patient anatomy 916, a digital surgical microscope ("DSM") CAMERA TARGET 920 (and associated reference frame), a DSM CAMERA TARGET 920a, 920b, and 920c (and associated reference frame) during camera calibration (a plurality of poses), a CAMERA OPTICAL MODEL REFERENCE FRAME viewing patient anatomy 922, a CAMERA OPTICAL MODEL REFERENCE FRAME during camera calibration (a plurality of poses) 922a, 922b, and 922c, and a LOCALIZER REFERENCE FRAME 924.

The example system 100 of FIG. 1 also includes a PATIENT ANATOMY REFERENCE FRAME OF PHOTOGRAMMETRY MODEL (also "patient anatomy reference frame") also "photogrammetry reference frame" 926, a PATIENT DATA REFERENCE FRAME (reference frame of patient volume data) 928, a patient frame (clamp) 930, a computer-vision readable target for scale and/or reference frame 940, a reference frame of computer-vision readable target (optional) 942, a CV-READABLE-TARGET_T_PATIENT-TARGET transformation 944, a PHOTOGRAMMETRY_T_PATIENT-DATA transformation 946, a calibration device 950, an object on calibration device 952, a computer-vision-readable target 954, a reference frame of the computer-readable-vision target 956, a feature on object on calibration device 958, a photogrammetry reference frame 960, a navigation target on calibration device 962, a reference frame of navigation target on calibration device 964, a CALIBRATION-TARGET_T_CV-READABLE-TARGET transformation 966, a PHOTOGRAMMETRY_T_CV-READABLE-TARGET transformation 968, and a PATIENT-TARGET_T_PATIENT-DATA transformation 970.

FIG. 4 illustrates a diagram of a calibrated stereoscopic camera in which the optical intrinsic and/or extrinsic parameters are fully characterized, according to an example embodiment of the present disclosure.

In some embodiments, as will be described further below in relation to FIG. 15, the navigation system 168 and the digital surgical microscope computer system 200 (also referred to as "visualization system") may be integrated as one system (e.g., as a single medical device). The integrated surgical navigation and visualization system may be used to perform one or more methods of patient registration described herein.

Example Registration Embodiment

Figures 1, 5B:
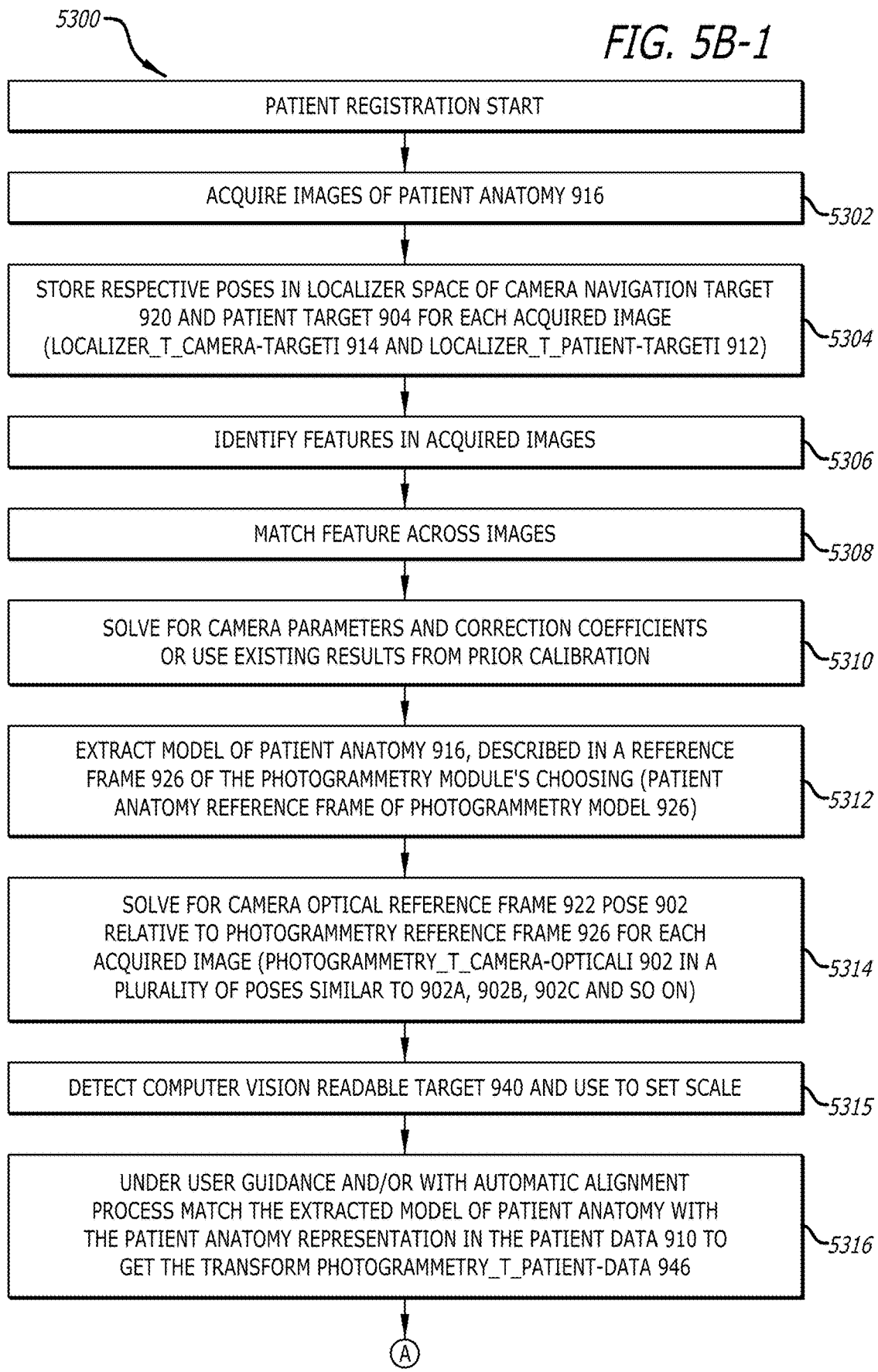
FIG. 5B illustrates an example procedure or routine for determining a camera calibration and a camera registration for the stereoscopic navigation systems of FIG. 1, according to an example embodiment of the present disclosure.

FIG. 5A illustrates an example procedure 5200 or routine for calibrating a camera and FIG. 5A illustrates an example procedure 5300 or routine for determining a patient registration for the stereoscopic navigation systems 100, according to an example embodiment of the present disclosure. Although the procedures 5200 and 5300 are described with reference to the flow diagram illustrated in FIG. 5A and FIG. 5B, it should be appreciated that many other methods of performing the steps associated with the procedures 5200 and 5300 may be used. For example, the order of many of the blocks may be changed, certain blocks may be combined with other blocks, and many of the blocks described are optional. For example, camera parameters may be determined before images are acquired or received.

Further, the actions described in procedures 5200 and 5300 may be performed among multiple devices including, for example, the digital surgical microscope computer system 200, the navigation computer system 170, the robotic arm 210, and/or the stereoscopic camera 130. For example, the procedures 5200 and 5300 may be performed by a program stored in the memory device that is communicatively coupled to or part of the digital surgical microscope computer system 200 or the navigation computer system 170.

The example procedures 5200 and 5300 represent similar functions and for the purposes of the following discussion the procedure 5300 is chosen as fully representative of both procedures. The example procedure 5300 is configured to automatically provide a touchless determination method for extracting locations of surface features from a live patient view in a certain reference frame, called herein variously the "PATIENT ANATOMY REFERENCE FRAME OF PHOTOGRAMMETRY MODEL" 926 or the "patient anatomy reference frame" 926 or the "photogrammetry reference frame" 926. The example procedure 5300 includes registering the patient anatomy reference frame 926 to a navigation frame 904 hereby called the patient target reference frame, where the patient target reference frame 904 is trackable by the first camera 105 (e.g., an NDI Polaris Vega localizer camera).

The procedure begins when the digital surgical microscope computer system 200 causes the stereoscopic camera 130 to automatically (or when necessary manually in a starting pose about a patient) move via the robotic arm 210 to a starting pose for acquiring an image of patient anatomy (block 5302). The digital surgical microscope computer system 200 then causes the stereoscopic camera 130 to move in an automated fashion via software program on its robotic arm 210 about the patient anatomy of interest 916, acquiring a snapshot at each relevant robot pose. Additionally acquired, received, and/or stored are the respective poses 914 and 912 in the reference frame 924 of localizer 105 of each the camera navigation target 920 and the patient target reference frame 904 (block 5304.) The patient anatomy 916 is fixed rigidly in the patient target reference frame 904 during the course of image acquisition. FIG. 1 shows a diagram of the patient target reference frame 904 relative to the patient anatomy 916. The camera 130 moves about the patient anatomy 916. The digital surgical microscope computer system 200 causes the robotic arm 210 to move in a path or set of paths about the patient such that the patient anatomy of interest 916 is viewed from a range of disparate angles such that a large proportion of the anatomy is captured in at least one snapshot (more is preferable) and ideally more than one angle. The path or paths are varied such that there is a fair amount of overlap (for example 75%) between each image and at least one other in the set of acquired or received images. To facilitate subsequent steps, which rely on image processing and computer vision techniques, a pose of the digital surgical microscope head is optionally moved into a more optimal focus position at each robot pose using a "robotic autofocus" technique: A control loop of the digital surgical microscope computer system 200 monitors the disparity and sharpness between the left and right eyes of the digital surgical camera 130 and attempts to drive that disparity to a local minimum (e.g. zero) and the sharpness to a local maximum by moving the robotic arm 210 such that the stereoscopic digital surgical microscope camera 130 moves nominally up and/or down along its ostensible optical axis 908.

Next, the digital surgical microscope computer system 200 receives and analyzes the acquired images using a photogrammetry module (e.g., 3dflow.net's Zephyr) to identify and/or characterize two-dimensional or three-dimensional features in each image which meet requirements to be usable in subsequent steps (block 5306). The photogrammetry module in the digital surgical microscope computer system 200 matches features across images, using the overlap between the images (block 5308). The photogrammetry module next solves for camera parameters and/or correction coefficients (block 5310). This includes solving for pinhole camera model intrinsic parameters including focal length and principal point, solving for camera model distortion correction coefficients, and solving for the pinhole camera model's extrinsic parameters (e.g., the position and orientation of the camera model reference frame 922 relative to the photogrammetry reference frame 926 to within a scale).

In some examples, the digital surgical microscope computer system 200 solves for camera parameters using photogrammetry as described. For photogrammetry a target object can be any object that retains its shape (what we will call being "rigid") over the course of the image acquisition, and has a minimal number of algorithm-friendly "features" dispersed over the surface of the object that the algorithm can detect in a minimal number of images. However, scale of the scene cannot be determined from a random object; a scale must be set either manually or in an automated way by inserting a scale object in the scene for example 940. The distance between two detectable landmarks of the scale object 940 are detected with computer vision algorithms in the acquired or received images, added to the photogrammetry model and used to set the scale of the entire model and all subsequent parameters found from said model (block 5315.)

The snapshot poses are overlapping such that a minimal number of features can be found in more than one image, and each image has a minimal number of such features (but not necessarily the same features across all images). Features are detected in each image (block 5306) using any of several well-known feature detection algorithms such as SIFT (scale invariant feature transform). The features detected as such are each characterized using a feature "descriptor", which allows that same feature to be detected in multiple images and the algorithm to know that it is the same feature. The pose in pixel space of each such feature in the associate image is recorded along with the feature descriptor; this pixel pose is used in the next step which is camera calibration, to assist in the determination of how features in the scene get projected via the camera structure to the sensor plane which converts the viewed scene into the images thus received.

With the assumption of the primary object in the scene (here the patient anatomy 916) being "rigid" or at least stationary over the image acquisition time, the algorithm is thus supplied with views from multiple poses of a given set of non-moving features. The features are matched across images (block 5308) such that a given feature is found in multiple views of the scene. This is repeated for different sets of features (typically a continually varying such set) over the set of received images. This information is used to solve for the parameters in a camera model. This is known as "camera calibration" (block 5310.)

Returning to FIG. 5B, the photogrammetry module in the digital surgical microscope computer system 200 establishes the photogrammetry reference frame 926 and determines the locations in said frame of the 2D features located above (block 5312). The photogrammetry module thereby converts the 2D features to 3D features in the form of a point cloud that samples the target surface to within a scale. In some embodiments, the 3D features are formed as a 3D model. Due to the ability to use any object (versus a calibration object of known structure), the scale of the world scene is not known at this point in the camera calibration using photogrammetry. Scale may be determined (as discussed below) by including an object of known dimensions in at least some of the images captured during acquisition (block 5315.) The object is then found manually or automatically in the 3D model and the corresponding model points. The photogrammetry reference frame 926 selected by the photogrammetry module is sufficient for the remainder of the tasks. However it can be beneficial to specify a coordinate system under some other specification. In this case the origin and axes of the reference frame are set in manner similar to how scale is found, for example by including a planar object such as 940 with linear orthogonal features that are used to define the X and Y axes; the Z axis is defined implicitly using the vector cross product of the X and Y axes, in a right-handed coordinate system 942 by convention as shown in the image.

The pose of the camera optical model reference frame 922 (and 922a, 922b, etc. for respective separate acquired or received images) relative to the photogrammetry reference frame 926 is solved for each acquired or received image (block 5314) (or for however many images are solvable.) In practice the solutions for such poses along with the patient anatomy model extraction (block 5312) and the camera calibration (block 5310) are solved simultaneously and iteratively in the photogrammetry module.

The patient data 910 is then registered to the patient anatomy 916 represented in the photogrammetry model 926 (block 5316). This amounts to determining the transformation 946 between the two reference frames 926 and 928. This transformation 946 is called PHOTOGRAMMETRY_T_ PATIENT-DATA. In some embodiments, the digital surgical microscope computer system 200 uses a function for finding a transformation required to align two point clouds, typically one from the target extracted as just described, and another generated from the patient scan data such as CT or MRI. Further, some such photogrammetry modules (including 3dflow.net's Zephyr) provide for "densifying" the point cloud using information available in the 2D images, as well as surface fitting techniques, to improve such transformation determination. Some modules including 3dflow.net's Zephyr provide for converting the densified point cloud into a 3D geometric mesh, using the colors available from the images to determine the color of a mesh vertex. Such a colored mesh is optionally exported for example in .OBJ format for use in later verification of the accuracy of target surface extraction and camera model intrinsic and extrinsic calculation. In some embodiments, the user is prompted to select a small number of corresponding points in each the patient anatomy photogrammetry model and the patient data. The registration transform 946 PHOTOGRAMME- TRY_T_PATIENT-DATA is then calculated with a "find optimal transformation" algorithm (ref http://nghiaho.com/?page_id=7).

The final steps for determining the patient registration 970 PATIENT-TARGET_T_PATIENT-DATA described in procedure 5300 rely on procedure 5200 having been completed. Thus we complete the description of those parts of procedure 5200 which differ from and/or extend procedure 5300. In some embodiments, all of the steps of procedures 5200 and 5300 are combined into a single procedure that happens after the patient is secured in the patient frame (e.g. clamp) 930. While this may seem like it could take longer than doing 5200 at some time prior to the patient being secured and then doing the slightly shorter procedure 5300 after patient securement, in practice as described earlier, often all the parameter solutions are solved simultaneously in the photogrammetry module. The procedures are separated here because it is an option to do so and by performing the camera calibration and registration procedure 5200 separately, connection to other existing surgical navigation systems is enabled which surgical systems provide their own patient registration procedure. The camera calibration and registration procedure 5200 with the addition of a subsequent stereo camera calibration step such as found in OpenCV's cv:stereoCalibrate routine also enables the use of the stereoscopic digital surgical microscope camera as a highly accurate measurement device.

The example camera calibration and registration procedure 5200 uses a calibration device 950 in place of patient anatomy 916. Blocks 5202, 5204, 5206, 5208, 5210, 5212 and 5214 correspond in function to blocks 5302, 5304, 5306, 5308, 5310, 5312 and 5314 described previously but with the calibration device 950 in the scene instead of the patient anatomy 916. Procedure 5200 connects the photogrammetry reference frame 950 to a navigation reference frame 964 (which is the reference frame of the navigation target 962; often the target and its reference frame are described as one and the same) as follows. A computer vision readable target 954 on the calibration device is detected in the acquired or received images and the locations of its salient features located relative to the photogrammetry reference frame 960 which salient features describe the X and Y axis of a reference frame 956 the Z axis of which reference frame is found through the double-cross method described elsewhere in this document. This is essentially equivalent to "patient registration" but for the calibration object 952 and is made possible by and differs in some embodiments from the registration of a live patient by this automated or semi-automated determination of the transformations 968 and 966 via the use of the computer vision readable target 954 and by design knowledge of the relative poses of the navigation target 962 and the computer vision readable target 954, and accurate precise manufacture of same. Such a method is made possible for the live patient case by the addition of such a computer vision readable target 940 to the patient frame (e.g. clamp) 930 to create 1000 plus a bridge device 1100 as will be described (shown in FIG. 8). The scale is set (block 5217) as in the patient registration case (block 5315) with the possible exception that in the camera calibration and registration case in procedure 5200, the scale can be set using the same target 954 used to determine the reference frame 956. A transformation 968 PHOTOGRAMMETRY_T_CV-READABLE-TARGET between the photogrammetry reference frame 960 and the computer vision readable target 954 is determined via the photogrammetry module and stored (block 5218.)

The transformation 966 CALIBRATION-TARGET_T_CV-READABLE-TARGET is known by design and/or found by measurement and is stored (block 5220.) Alternatively the transformation can be calculated from the photogrammetry model by locating the navigation targets and using design knowledge of their poses in their respective navigation reference frame. In this document where appropriate, "physical measurement" and "measurement" can be achieved by any established method including using a device such as a coordinate measuring machine (CMM) as well as by using photogrammetry.

The respective poses in each acquired or received image (or for however many are solvable) of the camera optical reference frame (922a, 922b, etc.) relative to the calibration device navigation target 964 are calculated according to the equation given in block 5222.

For each acquired or received image (or for however many are solvable) the stored poses (914a, 914b, etc., and 912a, 912b, etc.) in localizer space of the camera navigation target 920 (which in various poses become 920a, 920b etc.) and calibration device navigation target 964 are used to calculate the pose 900 CAMERA-TARGET_T_CAMERA-OPTICALi of the camera optical reference frame 922 relative to the camera target 920 (block 5224) where the subscript 'i' denotes an index into the plurality of acquired or received images for which this parameter is calculated.

A final pose 900 CAMERA-TARGET_T_CAMERA-OPTICAL is calculated (block 5226) by averaging the plurality of CAMERA-TARGET_T_CAMERA-OPTICAL transforms thus calculated and is stored as the final transform 900 CAMERA-TARGET_T_CAMERA-OPTICAL. This transform 900 CAMERA-TARGET_T_CAMERA-OPTICAL is utilizable in example patient registration procedure 5300 directly.

The final transform 900 CAMERA-TARGET_T_CAMERA-OPTICAL just calculated is necessary for the embodiment described in example patient registration procedure 5300. In some embodiments the patient registration is found without knowledge of the transform 900 CAMERA-TARGET_T_CAMERA-OPTICAL; this registration of patient anatomy reference frame 926 to navigation reference frame (patient target reference frame) 904 is achieved with a "dual reference frame bracket" 1000 also called variously a "hybrid photogrammetry "PG"/nav target". This method of connection also determines the scale of the photogrammetry results discussed above. In the example, the dual reference frame bracket 1000 comprises a set of navigation-trackable targets 1002, 1004, 1005 and 1006 (or more as desired) for the navigation method as well as a set of computer-vision trackable targets 1008, 1010 and 1012 for photogrammetry and/or computer vision based patient registration and calibration of the digital surgical microscope camera(s). The navigation-trackable targets compose the navigation target on the patient reference frame (the "patient target") 904 in this embodiment. The computer-vision trackable targets 1008, 1010 and 1012 compose the computer-vision readable target 940 and also define the reference frame 942 position and orientation. Patient registration is determined as a transformation 906 between the patient target reference frame 904 (as determined from the nav target) and the patient anatomy reference frame 926 (as determined from photogrammetry). Note that 940 and 904 when connected rigidly compose an equivalent to 1000 hybrid photogrammetry/navigation target.

As discussed herein, trackable targets include navigation device trackable targets such as a surgical tool or a clamp. Trackable targets may also include photogrammetry trackable targets which may include computer-vision-ready targets. Where appropriate and convenient, navigation-trackable targets and computer-vision trackable targets are differentiated from each other but it is understood that in many instances they are interchangeable with an associated change in tracking camera and/or tracking method. To track a tool of interest (such as a clamp holding patient anatomy) the systems disclosed herein may include a trackable target mounted on a tool. The trackable target might consist of a geometric arrangement of markers such as retroreflective spheres capable of reflecting infrared ("IR") light, or of a similar arrangement of IR light emitters. These are detected by a localizer device 105 with an IR-detecting camera, and when required an (IR) light source to reflect off the retroreflectors and/or to stimulate a passively-synchronized IR emitter. Actively-synchronized IR emitters also exist. Alternatively the trackable target might consist of computer-vision readable targets created from high-contrast patterns, or by patterns that reflect or emit light in various regions of the electromagnetic spectrum.

To facilitate the determination of scale in a photogrammetry-solved scene, as well as to provide other means of communicating information to digital surgical microscope computer system 200, computer-vision-ready targets such as April tags or ArUco targets are used. A given photogrammetry tool might also provide recommended targets to use, which targets the tool is optimized to recognize. These targets are high-contrast and contain strong edges and unique patterns encoding some amount of digital bits of information. By using standard target sizes and shapes known prior to use, the origin and reference frame orientation are known quite accurately (typically below 0.1 mm depending on reproduction method used to "print" the target).

Using three such targets as 1008, 1010 and 1012 to define respectively the origin of a right-handed coordinate reference frame 942, a point on the x axis a known distance away from the origin, and a point on the y axis a known distance away from the origin, the digital surgical microscope computer system 200 detects not only the location and orientation of said reference frame 942 but also the scale of the whole photogrammetry model. In a further step similar to block 5220, the transform between the said computer vision readable target reference frame 942 and the patient anatomy reference frame of the photogrammetry model 926 is determined by reading the pose of 942 in the photogrammetry model giving the transform COMPUTER-READABLE-TARGET_T_PHOTOGRAMMETRY. With knowledge via design and/or measurement of the locations of the navigation targets 1002, 1004, 1005 and 1006 (or more as desired) relative to reference frame 942 we have PATIENT-TARGET_T_COMPUTER-READABLE-TARGET. Then the patient registration 906 is calculated:

PATIENT-TARGET_*T*_PHOTOGRAMMETRY=PATIENT-TARGET_*T*_COMPUTER-READABLE-TARGET*COMPUTER-READABLE-TARGET_*T*_PHOTOGRAMMETRY

This completes the alternate embodiment of finding the patient registration.

The locations of the navigation trackable markers 1002, 1004, 1005 and 1006 in the reference frame of the bracket 1000 are known by design and/or by measurement and together compose a tool described by the markers' geometric relation to each other in that reference frame. This information is stored in a tool description file and used by the navigation computer 170 to discern which tool is in view of the localizer 105 and in what pose relative to the localizer's reference frame 924.

The locations of the computer-vision readable targets 1008, 1010 and 1012 are also known by design and/or by measurement, in the same reference frame as the navigation markers, namely that of the bracket. Such CV-ready targets are detectable as unique regardless of viewing angle, and encode a known origin for example the physical center of the pattern. Other embodiments may loosen such restrictions for example by allowing viewing-angle redundant individual targets as long as the group of targets is detectable as unique regardless of viewing angle.

While it is convenient to use physical patient features to position and orient reference frames, the reference frames can be considered virtual since they do not need to correspond to a physical structure but can be located anywhere in space. This is often the case in the photogrammetry default reference frame 926.

Figure 7:
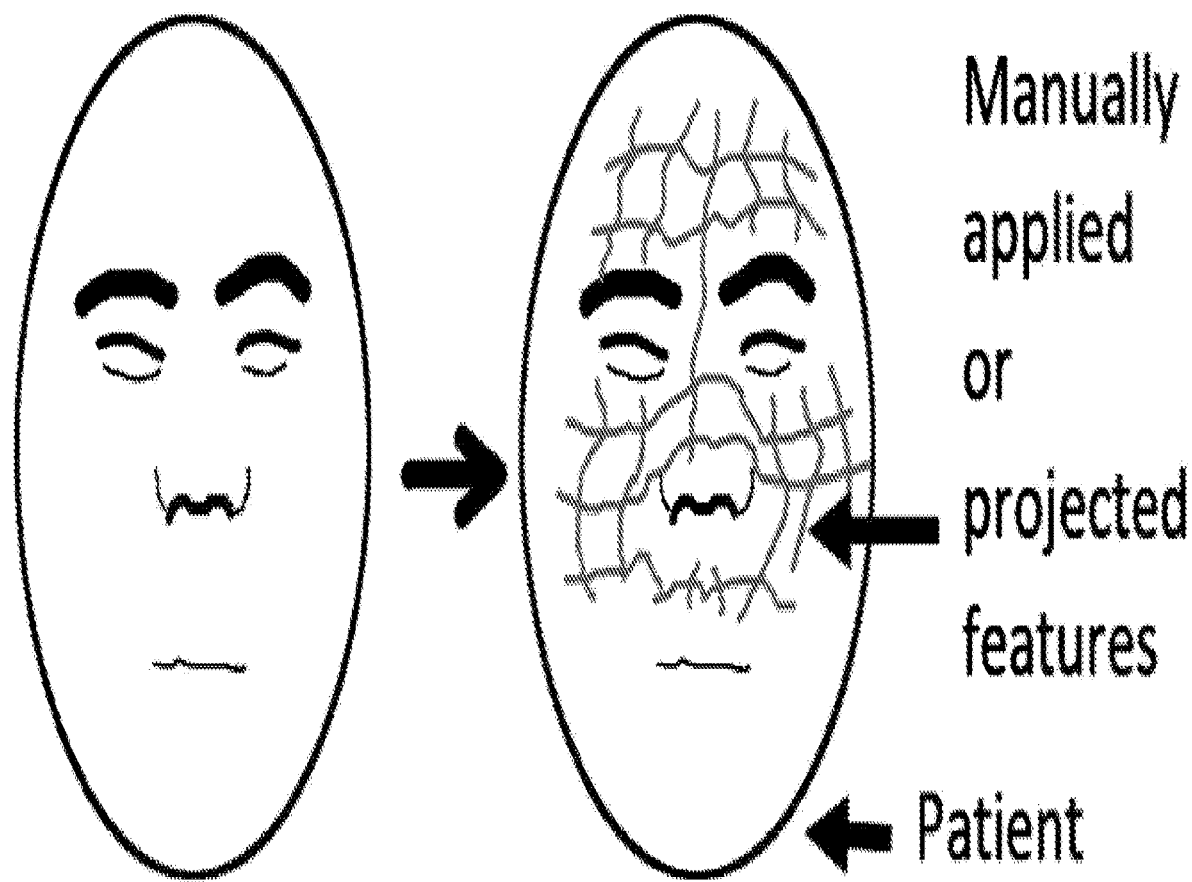
FIG. 7 is a diagram of features added to a patient, according to an example embodiment of the present disclosure.

Photogrammetry relies on the patient anatomy of interest 916 containing detectable features. In some situations there are not enough such features. This is mitigated in one of several ways, depending on user preference and patient condition. FIG. 7 is a diagram of features added to a patient, according to an example embodiment of the present disclosure. For example, features may be manually added (e.g. by drawing on the patient anatomy manually using easily removed surgical markers such as Viscot 1444-30 EZ Removable Ink® markers https://www.viscot.com/products/green-ez-ink/). In another example, a multitude of thin textured stickers may be affixed onto the patient temporarily or a thin high-contrast material such as baby powder may be applied in random speckles over the patient anatomy. Also, a textured thin material may be placed over the patient such as gauze or specialized thin drape or a texture may be projected onto the patient using an image projector mounted rigidly relative to the patient, for example one or more laser projectors mounted in the operating room. The microscope light is adjusted (for example, reduced) to facilitate detection of the laser texture. Alternatively, the wavelength(s) of the projectors used is/are adjusted to fall outside of the visible spectrum such as a near infrared wavelength in the approximate range 750-900 nm. Such a technique is used in depth sensor cameras such as Intel's RealSense camera. In the alternative, the camera 130 may contain a filter wheel to allow detection across only a select near infrared spectrum, where the texture projector wavelength is matched to this filter when used. In furtherance of above, an additional registration step may be performed using a fixed object that allows photogrammetry camera calibration and registration in both the visible and NIR regimes, thus enabling the calculation of any transformation owing to optical differences between the two regimes. This is then used to transform the pose of the patient surface captured in NIR into the equivalent surface located in the visible spectrum. In most cases, any augmentation done to the patient anatomy is removed or neutralized after successful image acquisition and before the processing proceeds.

Figure 8:
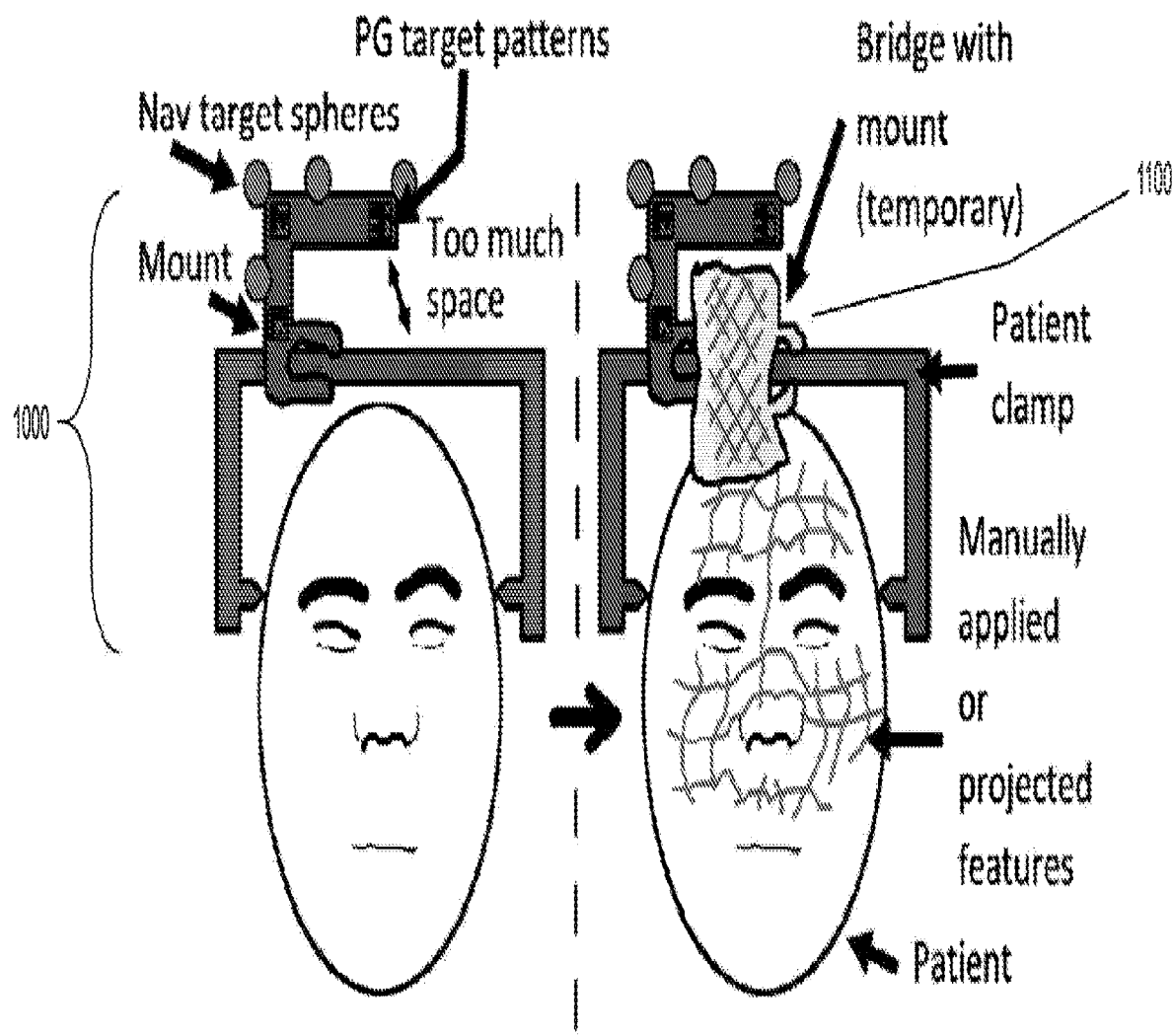
FIG. 8 is a diagram that shows how the bridging may occurring, according to an example embodiment of the present disclosure.

Returning to FIG. 5, the registration step 5300 may be performed by bridging a gap between patient anatomy and a navigation/PF target. FIG. 8 is a diagram that shows how the bridging may occurring, according to an example embodiment of the present disclosure. The hybrid PG/nav target may be captured in the same reference frame as patient anatomy of interest. For easiest use, this means that the PG may be able to "connect" the region containing the target and anatomy by being able to detect features of interest in images that overlap sufficiently for PG while spanning the space between the two regions.

For the simple case shown in FIG. 8, image overlap and span is easily achieved because the target is physically close enough to the patient anatomy. The more general case is where, to remain visible to the navigation camera 130, the navigation trackable portion of the target must be mounted physically farther from the patient anatomy. This is solved by placing rigidly a temporary "bridge" structure 1100 between part of the patient anatomy outside the region of interest and the hybrid target 1000 such that sufficient overlap between consecutive images is possible during acquisition while still allowing the patient anatomy and the computer vision readable target to be imaged completely. The bridge has on its surface features and/or texture of the sort the photogrammetry can readily use.

The need for a bridge is mitigated by moving to a different navigation input such as that used in U.S. Provisional Application No. 63/086,310, titled "Auto-Navigating Digital Surgical Microscope", the contents of which are incorporated herein by reference. Auto-navigation enables targets to be placed closer to the patient, because the line of sight from navigation camera to the navigation trackable target(s) is significantly shorter and more direct.

Figure 13:
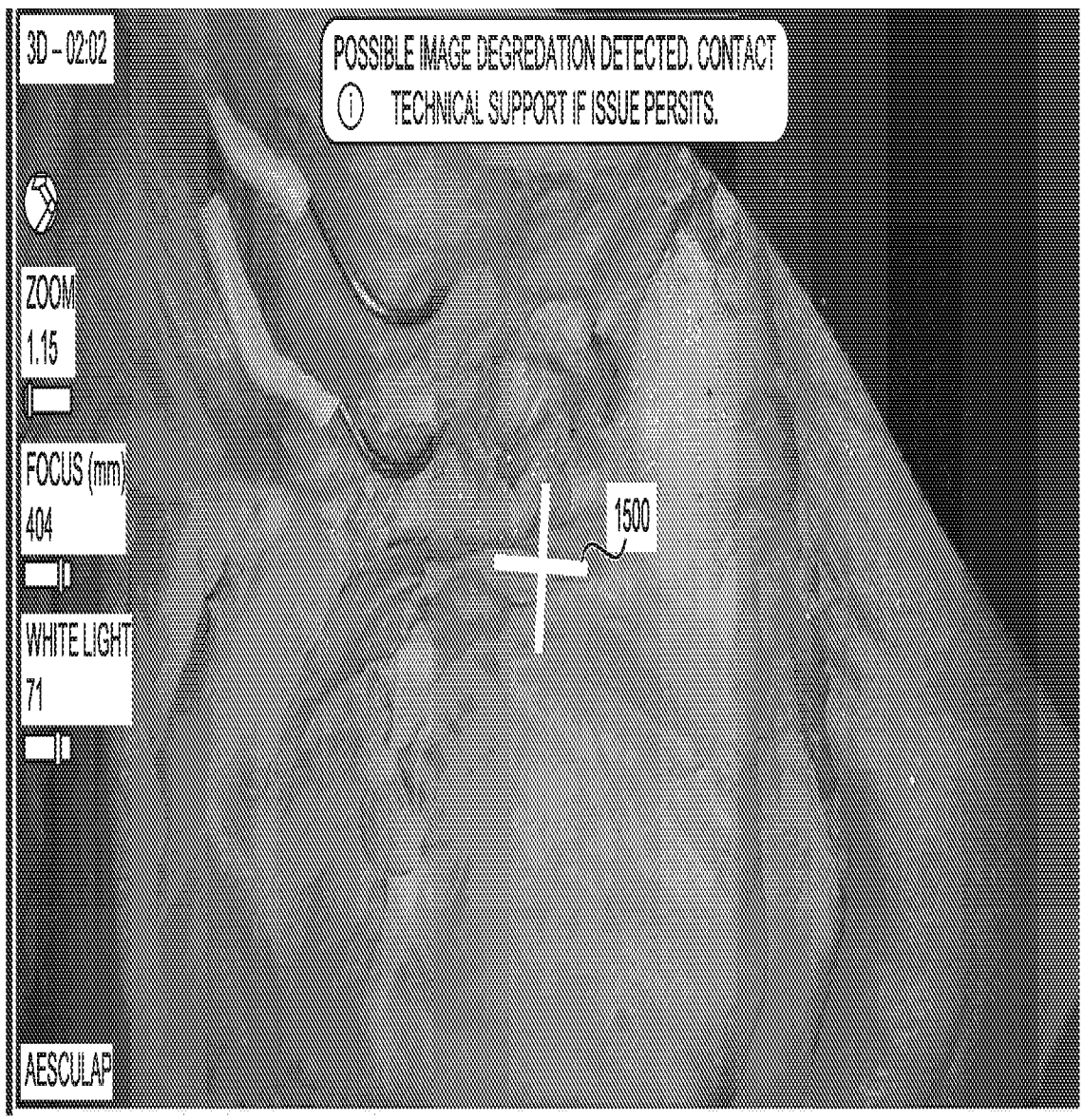
FIGS. 13 and 14 are diagrams showing a live surgical view (FIG. 13) and patient data overlaid said live surgical view (FIG. 14) using the system, methods, and apparatus discussed herein.
Figure 14:
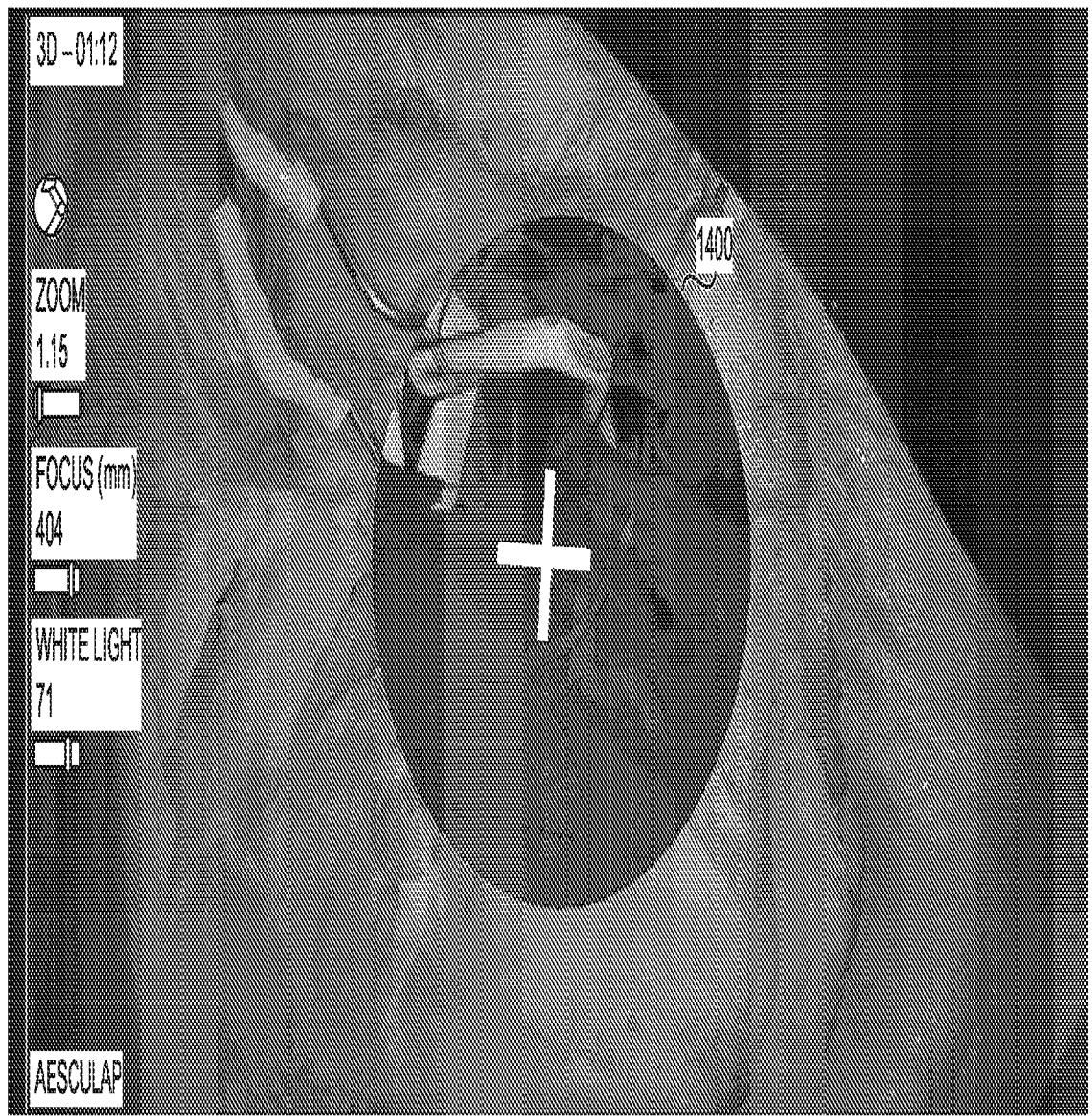

FIGS. 13 and 14 show diagrams of patient preoperative data 1300 and 1400 overlaid on a current stereoscopic view. In FIG. 13, the preoperative data 1300 includes a target indicator. In FIG. 14, the preoperative data 1400 includes a blue-colored overlay showing blood vessel location under the skin, where the same blood vessels are not visible in FIG. 13 by comparison. This overlay enables a surgeon to see through solid objects in place where they are operating instead of having to look over at a separate surgical navigation display and then remember what they saw and try to assimilate it back onto the live view . . . thus they can make faster and make more informed incision decisions.

In one embodiment, the camera of the digital surgical microscope is used as the localizer thereby eliminating the need for a separate localizer. This novel approach also eliminates (by reducing to identity) the need to determine two transformations in the enablement of augmented reality: CAMERA-TARGET_T_CAMERA-OPTICAL and LOCALIZER_T_CAMERA-TARGET. This is because the localizer is now the camera and no camera target is needed, and additionally the localizer coordinate system is chosen to be coincident with the camera optical coordinate system. When feasible, patient anatomy features are used as navigation targets, which further eliminates the need for the determination of the transformation PATIENT-TARGET_T_PATIENT-DATA since the features are already coincident. When this is not feasible, fiducials or other targets are added to the patient anatomy and registered in a manner similar to other embodiments described herein.

Stereogrammetry Embodiment

Stereogrammetry ("SG") is optionally used for surface extraction as an alternative to photogrammetry because SG can use template matching to detect surface points instead of needing larger more robust features; template matching works on pixel differences/similarities, not gross feature differences/similarities. Texture is still required, but the need is reduced, and projected texture(s) if needed do not need to remain fixed in position and orientatoin on the patient during the entire image acquisition time; the texture only need to stay stationary during each single image acquisition time. As such a texture projector is affixed when needed to the digital surgical microscope head pointing out at the scene and moves with the head to each new pose during image acquisition. Line of sight problems are eliminated in this configuration. As in photogrammetry, various wavelengths/spectra of projector and detector (image sensor) configurations are available for use to match the operating requirements.

Below is a procedure for patient anatomy surface extraction using stereogrammetry:

1. Using the photogrammetry tool, calibrate each camera eye of the stereoscopic digital surgical microscope simultaneously using the same rigid target, which target has sufficient features to facilitate the PG solution; to avoid texture/feature insufficiency as might arise using a live patient, a specialized non-patient target is typically used.
2. Calculate the stereoscopic camera calibration parameters using the results of the single-camera calibration just obtained, along with an algorithm such as OpenCV: stereoCalibrate.
   a. Calculate the connection between the original PG camera spaces and the stereoCalibrate stereo camera calibration space. For example the reference frame of the stereo camera is defined as being coincident with that of the left camera eye, and the transformation to the right camera eye is known as a result of the stereoCalibrate function.
3. Use stereogrammetry to scan the patient anatomy surface, the hybrid target 1000, and whatever "bridge" 1100 exists between the two when such a bridge is needed.
   a. As in photogrammetry, the limited field of view of the stereoscopic camera requires that a multitude of overlapping images be acquired (or received) and a means of correlating adjacent images implemented. In stereogrammetry this is done using surface matching to align the surface found in one image to that found in the subsequent image.
   b. Also as in photogrammetry, texture is required but for slightly different reasons as described elsewhere; if texture is deemed necessary (as determined by training and/or algorithm/heuristic, a texture is provided to the patient anatomy surface using one of the techniques described elsewhere, with texture projection from a projector mounted on the microscope head the preferred method.

The computer vision readable targets 1008, 1010 and 1012 on the hybrid target 1000 are imaged as part of the stereogrammetry acquisition and their locations in the reference frame of the stereoscopic camera found. Using the connection between the stereoscopic camera reference frame and that of the photogrammetry camera reference frames, we now calculate the location of the hybrid target 1000 in photogrammetry space and end up with the equivalent information that we obtained using photogrammetry alone.

Robotic Arm Embodiment

Figure 9:
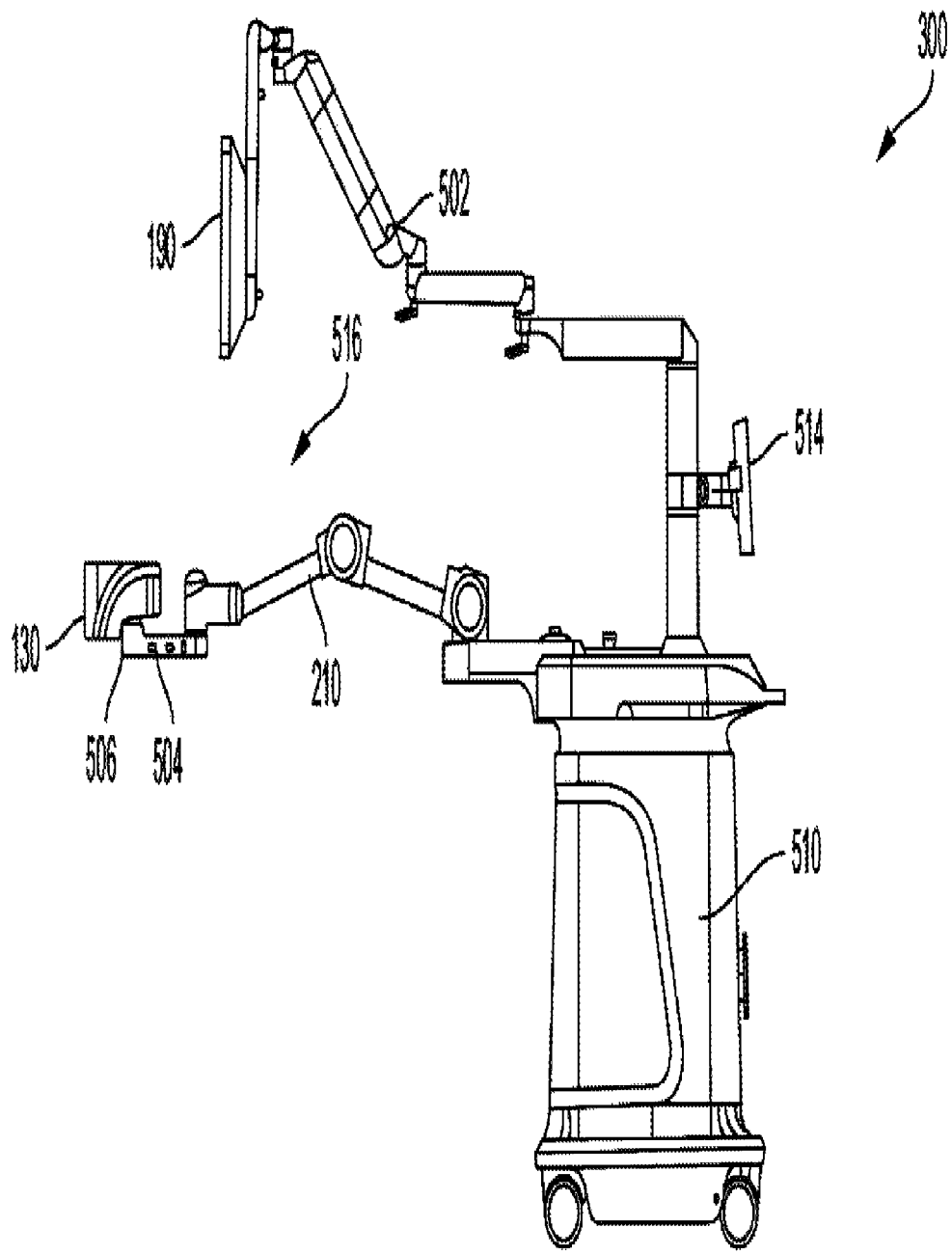
FIG. 9 shows a side view of the navigation system of FIG. 2, according to an example embodiment of the present disclosure.

FIG. 9 shows a side view of the stereoscopic navigation system 100 of FIGS. 1 to 3, according to an example embodiment of the present disclosure. In the illustrated example, a display monitor 190 may be connected to a cart 510 via a mechanical arm 502 with one or more joints to enable flexible posing. In some embodiments, the mechanical arm 502 may be long enough to extend over a patient during surgery to provide relatively close viewing for an operator. The cart 510 may house the navigation computer system 302 of FIG. 2.

As shown in FIG. 9, the display monitor 190 is posed within a surgical environment to be easily within an operator's line of sight while performing surgery on a patient. This flexibility enables the operator to place display monitors based on personal preferences or habits. In addition, the flexibility and slim profile of the stereoscopic camera 130 reduces area consumed over a patient. The example stereoscopic visualization platform accordingly operates as an extension of the operator's eyes, enabling the operator to perform microsurgeries without dealing with the stress, restrictions, and limitations induced by previous known visualization systems.

FIG. 9 also illustrates a side view of a stereoscopic robotic platform 516, including the stereoscopic camera 130 and the robotic arm 210 of FIG. 2. The stereoscopic camera 130 is mechanically coupled to the robotic arm 210 via a coupling plate 504. In some embodiments, the coupling plate 504 may include one or more joints that provide for further degrees of positioning and or orientation of the stereoscopic camera 130. In some embodiments, the coupling plate 504 has to be manually moved or rotated by an operator. For example, the coupling plate 504 may have a joint that enables the stereoscopic camera 130 to be posed quickly between having an optical axis along a z-axis (i.e., pointing downward toward a patient) and an optical axis along an x-axis or y-axis (i.e., pointing sideward toward a patient).

The example coupling plate 504 may include a sensor 506 configured to detect forces and/or torques imparted by an operator for moving the stereoscopic camera 130. In some embodiments, an operator may pose the stereoscopic camera 130 by gripping the control arms (discussed below). After the operator has clutched the control arms with their hands, the operator may position and/or orient the stereoscopic camera 130 with assistance from the robotic arm 210. The sensor 506 detects a force vector or torque angle provided by the operator. The example stereoscopic robotic platform 516 disclosed herein uses the sensed force/torque to determine which joints of the robotic arm 210 should be rotated (and how quickly the joints should be rotated) to provide assisted movement of the stereoscopic camera 130 that corresponds to the forces/torques provided by the operator. The sensor 506 may be located at an interface between the coupling plate 504 and the stereoscopic camera 130 for detecting the forces and/or torques imparted by an operator via the control arms.

In some embodiments, the sensor 506 may include, for example, a six degrees of freedom haptic force-sensing module. In these embodiments, the sensor 506 may detect translational force or motion in the x-axis, y-axis, and z-axis. The sensor 506 may also separately detect rotational force or motion around a yaw-axis, a pitch-axis, and a roll-axis. The decoupling of the translational force and the rotational force may enable the stereoscopic robotic platform 516 to more easily calculate direct and/or reverse kinematics for control of the robot arm 210.

The example sensor 506 may be configured to detect force since the robotic arm 210 may not be movable by an operator alone. Instead, the sensor 506 detects translational and rotational force applied by an operator, which is used by the navigation computer system 302 and/or the stereoscopic robotic platform 516 to determine which joints to rotate to provide assisted movement control of the robotic arm 210. In other examples, the robotic arm 210 may permit operator movement without assistance, or at least initial assistance. In these other examples, the sensor 506 detects motion imparted by the operator, which is used by the navigation computer system 302 and/or the stereoscopic robotic platform 516 to subsequently cause one or more joints to rotate, thereby providing assisted movement.

In the illustrated embodiments, a first end of the robotic arm 210 is mounted to the cart 510 while a second, opposite end of the robotic arm is mechanically connected to stereoscopic camera 130 (e.g., the robot end effector). FIG. 9 shows the robotic arm 210 holding the stereoscopic camera 130 in an extended pose, such as posing the stereoscopic camera 130 above a surgical site while keeping the rest of the stereoscopic robotic platform 516 out of the way of an operator. The cart 510 is configured to securely hold the stereoscopic robotic platform 516 and is weighted and balanced to prevent tipping under prescribed operating configurations.

Figure 10:
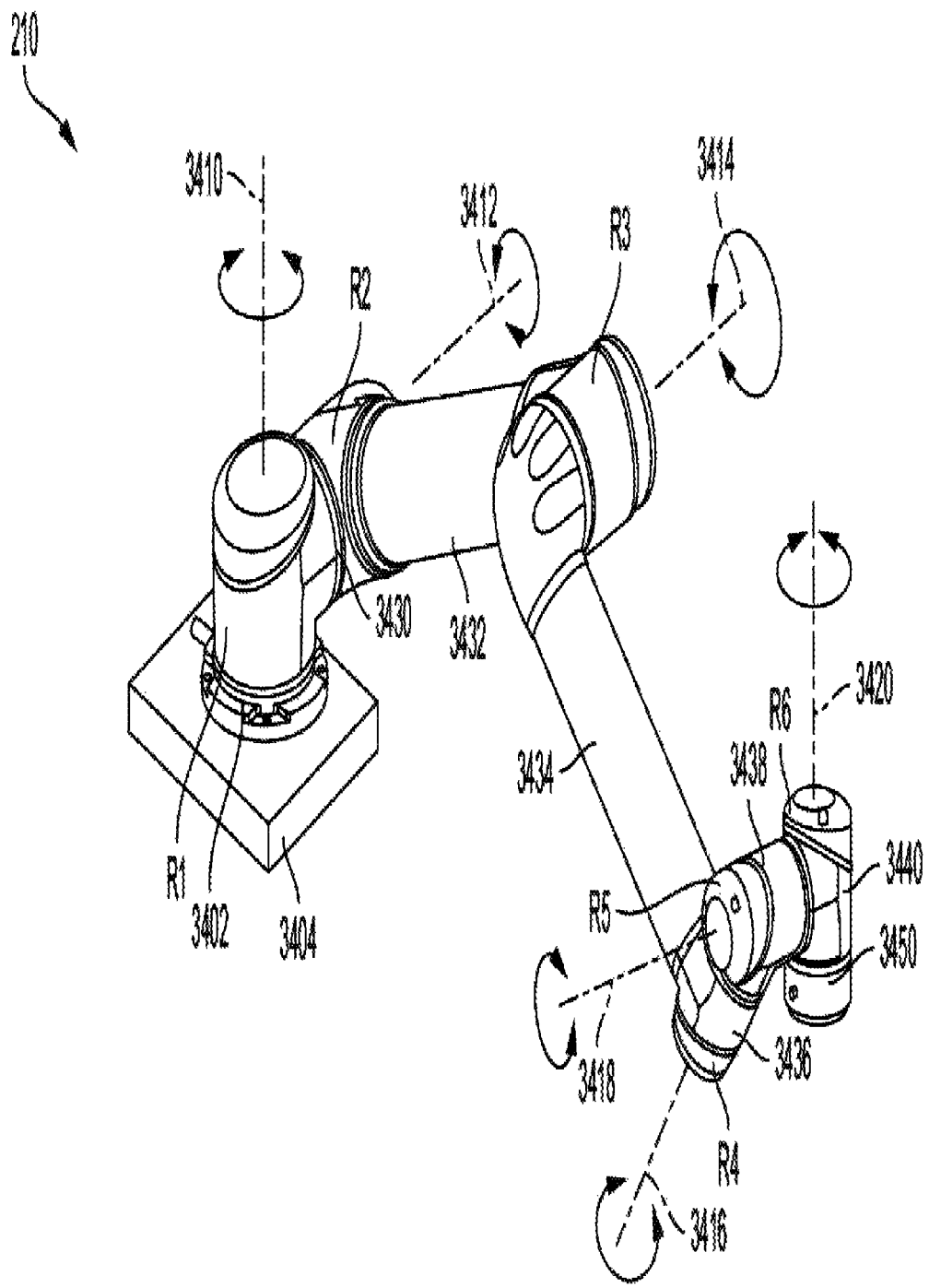
FIG. 10 illustrates an embodiment of an example robotic arm of the navigation system of FIG. 2, according to an example embodiment of the present disclosure.

FIG. 10 illustrates an embodiment of the example robotic arm 210, according to an example embodiment of the present disclosure. In some embodiments, the robotic arm 210 is similar to or comprises model UR5 from Universal Robots S/A. The exterior surfaces of the robotic arm 210 comprise aluminum and plastic materials, which are compatible for use in an operating room and easily cleaned.

In some embodiments, the robotic arm 210 may include mechanically or electronically locking brakes on the joints. The brakes may be engaged once the aim or "pose", which is generally the location and direction, of the stereoscopic camera 130 after it is set by an operator. The robotic arm 210 may include a locking or unlocking switch or other input device to prevent undesired manual or accidental motion. When locked, the example robotic arm provides sufficient stability that enables the stereoscopic camera 130 to provide a stable, clear image. The robotic arm 210 may additionally or alternatively include one or more dampening devices to absorb or attenuate vibrations following movement of the stereoscopic camera 130 to a new pose.

In the illustrated embodiment of FIG. 10, the robotic arm 210 includes six joints, labeled R1, R2, R3, R4, R5, and R6. In other embodiments, the robotic arm 210 may include fewer or additional joints. Additionally, in some embodiments, at least some of the joints R1 to R6 have rotational motion capabilities of +/−360°. The rotational motion may be provided by an electromechanical subsystem that includes, for each joint, an electric motor configured to drive a mechanical rotational joint through one or more anti-backlash joint gearboxes. Each of the joints R1 to R6 may include one or more rotational sensors to detect joint angular position. Further, each joint may include a slip clutch and/or an electromechanical brake.

Joint R1 includes a base joint that is mechanically coupled to a flange 3402, which is secured to a stationary structure 3404. The flange 3402 may include any type of mechanical connector. The stationary structure 3404 may include, for example, the cart 510 of FIG. 9, a wall, a ceiling, a table, etc. The joint R1 is configured to rotate around a first axis 3410, which may include the z-axis.

Joint R1 is connected to joint R2 via a link 3430. The example link 3430 includes a cylinder or other tubular structure configured to provide structural support for the downstream sections of the robotic arm 210. The link 3430 is configured to provide a rotational secure connection with joint R2 to enable joint R2 to rotate while the link 3430 is held in place by its connection to the joint R1. Joint R2 may include, for example, a shoulder joint configured to rotate around an axis 3412. The example axis 3412 is configured to be perpendicular (or substantially perpendicular) to axis 3410. The axis 3412 is configured to be within an x-y plane given the rotation of the joint R1 around the z-axis.

Joint R2 is mechanically coupled to joint R3 via link 3432. The link 3432 is configured to have a greater length than the link 3430 and is configured to provide structural support for downstream portions of the robotic arm 210. Joint R3 may include, for example, an elbow joint. Together with joint R2, joint R3 provides extensible positioning and/or orientating of the robotic arm 210. The joint R3 is configured to rotate around an axis 3414, which is perpendicular or orthogonal to the axis 3410 and parallel to the axis 3412.

Joint R3 is connected to joint R4 via link 3434, which provides structural support for downstream portions of the robotic arm 210. The example joint R4 may be, for example, a first wrist joint configured to provide rotation around axis 3416, which may be orthogonal to the axes 3412 and 3414. Joint R4 is mechanically connected to joint R5 via link 3436. Joint R5 may be a second wrist joint configured to provide rotation around an axis 3418, which is orthogonal to axis 3416. Joint R5 is mechanically connected to joint R6 via link 3438. Joint R6 may be a third wrist joint configured to rotate around axis 3420, which is orthogonal to the axis 3418. Together, the wrist joints R4 to R6 provide precise flexibility in posing the stereoscopic camera 130 described herein.

The example robotic arm 210 includes a connector 3450. The example connector 3450 is connected to joint R6 via link 3440. In some embodiments, the example link 3440 may include a sleeve that enables joint R6 to rotate the connector 3450. As discussed herein, the connector 3450 (located at the end-effector of the robotic arm 210) may be configured to mechanically couple to the coupling plate 504 or the stereoscopic camera 130 directly when a coupling plate is not used. The connector 3450 may include one or more screws to secure the robotic arm 210 to the coupling plate 504 and/or the stereoscopic camera 130.

In some embodiments, the robotic arm 210 of the illustrated example may have a maximum reach of 85 mm, in an orientation roughly similar to a human arm. The robotic arm 210 may have a payload capacity of 5 kilograms. Further, the robotic arm 210 may be configured as a "collaborative" device to enable safe operation in the proximity of humans.

Figure 11:
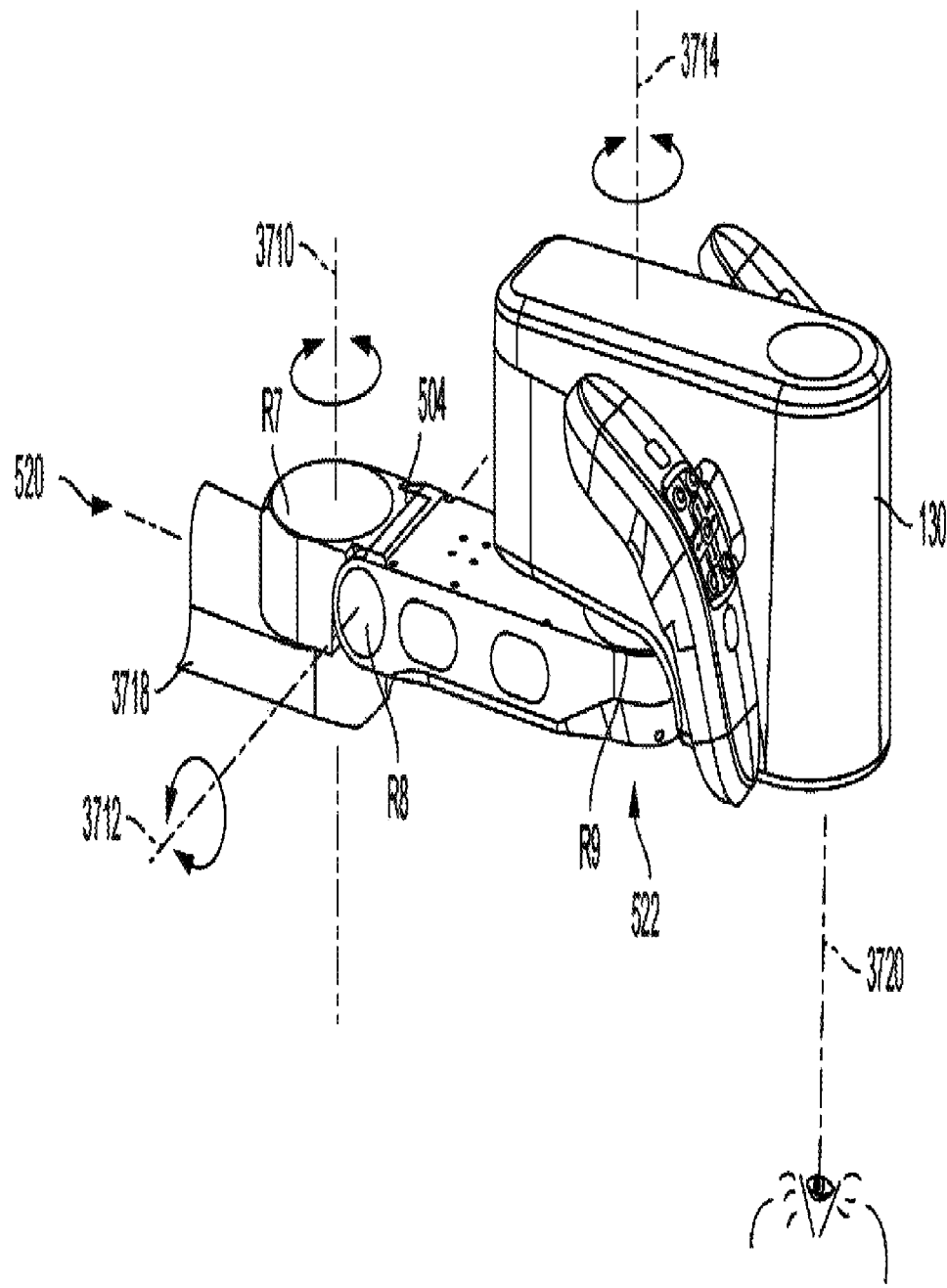
FIG. 11 illustrates an example orientation of the robotic arm and a stereoscopic camera using an optional coupling plate, according to example embodiments of the present disclosure.

FIGS. 10 and 11 illustrate example configurations of the robotic arm 210 and the stereoscopic camera 130, according to example embodiments of the present disclosure. FIG. 5A shows an embodiment of the coupling plate 504. In the illustrated example, a first end 520 of the coupling plate 504 is connected to the connector 3450 of the robotic arm 210. A second end 522 of the coupling plate 504 is connected to the stereoscopic camera 130. The example coupling plate 504 is configured to provide additional degrees of freedom for moving the stereoscopic camera 130. The coupling plate 504 also extends the maximum reach of the robotic arm 210. The coupling plate 504 may have a length between 10 cm to 100 cm.

The coupling plate 504 may include one or more joints. In the illustrated example, the coupling plate 504 includes joints R7, R8, and R9. The example joints are mechanical joints that provide rotation around respective axes. The joints R7 to R9 may comprise rotatable latching mechanisms that are movable after an operator actuates a release button or lever.

Surgical Navigation Computer Embodiment

Figure 12:
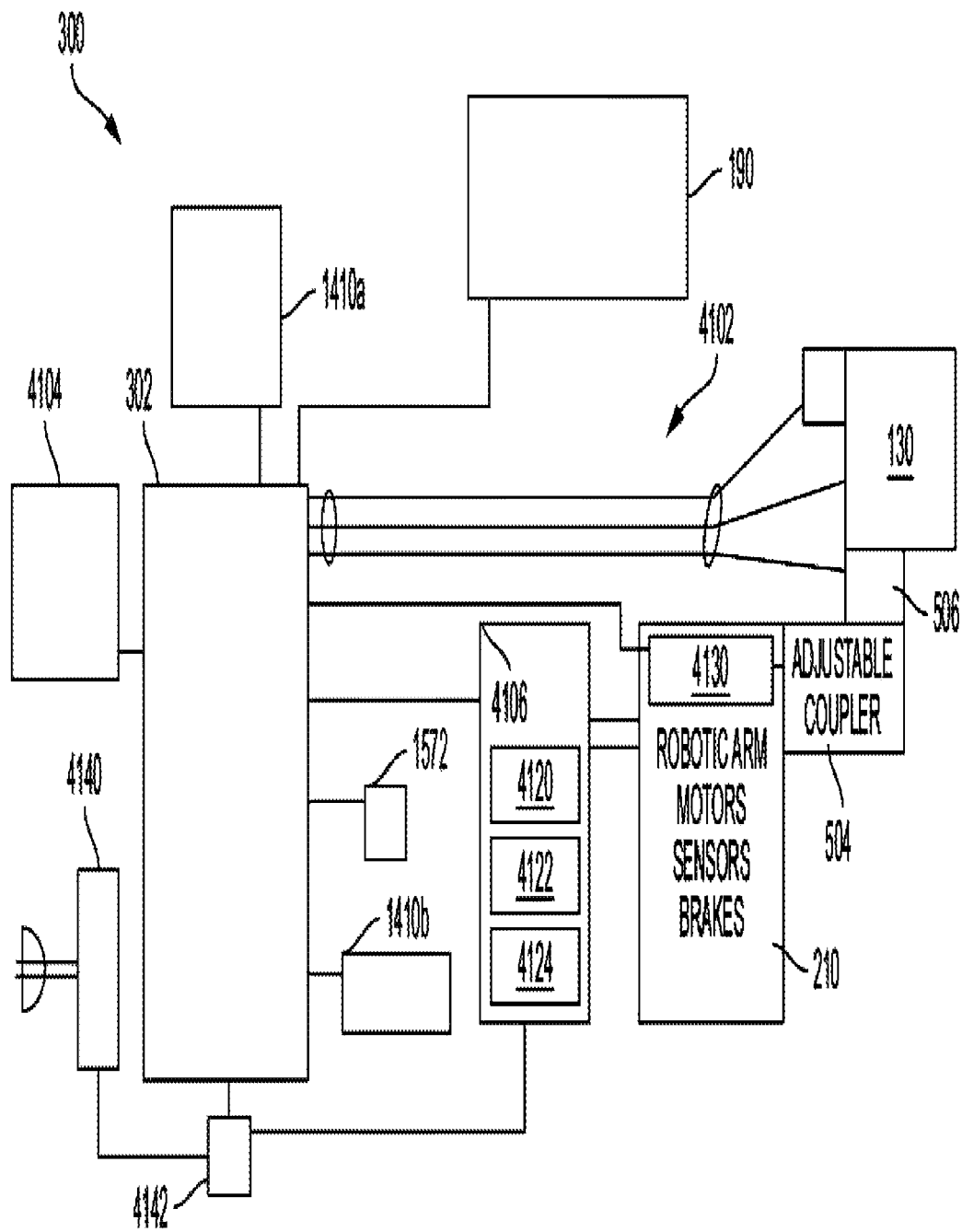
FIG. 12 illustrates an embodiment of the stereoscopic navigation system of FIGS. 1 to 11, according to an example embodiment of the present disclosure.

FIG. 12 illustrates an embodiment of the stereoscopic navigation system 100 of FIGS. 1 to 11, according to an example embodiment of the present disclosure. The example stereoscopic navigation system 100 includes the stereoscopic camera 130. In the illustrated embodiment, the stereoscopic navigation system 100 includes the navigation computer system 302, which is located remote from the stereoscopic camera 130. The navigation computer system 302 may include, for example, a processor, a laptop computer, a workstation, a desktop computer, a tablet computer, a smartphone, etc., configured with one or more software programs defined by instructions stored in a memory 1570 that, when executed by the navigation computer system 302, cause the navigation computer system 302 to perform the operations described herein. The example navigation computer system 302 in this example is configured to include (or perform the operations described in connection with) an information processor module 1408, an image sensor controller 1502, and/or a motor and lighting controller 1520.

The navigation computer system 302 is electrically and/or communicatively coupled to the stereoscopic camera 130 via a wire harness 4102. In some embodiments, the harness 4102 may be external to the robotic arm 210. In other embodiments, the wire harness 4102 may be internal or routed through the robotic arm 210. In yet other embodiments, the stereoscopic camera 130 may communicate wirelessly with the navigation computer system 302 via Bluetooth®, for example. The example navigation computer system 302 is also electrically and/or communicatively coupled to the sensor 506 via the wire harness 4102.

In the illustrated example, the navigation computer system 302 is further communicatively coupled to at least one of a display monitor 190, input devices 1410a, 1410b, and other devices/systems 4104 (e.g., medical imaging devices such as an X-ray machine, a CT machine, an MRI machine, a camera, a workstation for storing images, or surgical guidelines, etc.). The input device 1410a may include a touch screen device, and the input device 1410b may include a foot switch. The touch screen input device 1410a may be integrated with the display monitor 190 and/or provided as a separate device on, for example, the cart 510 of FIG. 9. The example display monitor 190 is configured to display one or more user interfaces that include a stereoscopic video (or separate two-dimensional left and right videos) of a target surgical site imaged by the stereoscopic camera 130.

The touch screen input device 1410a is configured to provide one or more user interfaces for receiving user inputs related to the control of the stereoscopic camera 130, the coupling plate 504, and/or the robotic arm 210. The input device 1410a may include one or more graphical control buttons, sliders, etc., that are configured to enable an operator to specify, set, or otherwise provide instructions for controlling a working distance, focus, magnification, source and level of illumination, filters, and/or digital zoom of the stereoscopic camera 130.

The example foot plate input device 1410b may include, for example, a food pedal configured to receive inputs for controlling a pose of the stereoscopic camera 130, the coupling plate 504, and/or the robotic arm 210. For example, the foot plate input device 1410b may include controls for moving the stereoscopic camera 130 along the x-axis, the y-axis, and/or the z-axis.

In other embodiments, the stereoscopic navigation system 300 may include additional and/or alternative input devices 1410, such as a joystick, mouse, or other similar 2D or 3D manual input device. The alternative input devices 1410 are configured to provide inputs similar to an X-Y panning device, with additional degrees of freedom resulting in flexibility of system motion. Input devices with 3D capabilities, such as a 3D mouse or six degrees of freedom controller are well suited for flexible and convenient input commands. Optionally, the alternative input devices 1410 may include a head, eye, or glasses-mounted tracking device; a voice recognition device; and/or a gesture input device. These types of alternative input devices 1410 facilitate "hands-free" operability such that an operator does not need to touch anything with their sterile gloves.

In the illustrated example, the stereoscopic navigation system 100 of FIG. 12 includes a robotic arm controller 4106 that is configured to control the robotic arm 210 and/or the coupling plate 504. The robotic arm controller 4106 may include a processor, a server, a microcontroller, a workstation, etc., configured to convert one or more messages or instructions from the navigation computer system 302 into one or more messages and/or signals that cause any one of joints R1 to R9 to rotate. The robotic arm controller 4106 is also configured to receive and convert sensor information, such as joint angular position and/or speed from the robotic arm 210 and/or the coupling plate 504 into one or more messages for the navigation computer system 302.

In some embodiments, the robotic arm controller 4106 is configured as a stand-alone module located between the navigation computer system 302 and the robotic arm 210. In other embodiments, the robotic arm controller 4106 may be included within the robotic arm 210. In yet other embodiments, the robotic arm controller 4106 may be included with the navigation computer system 302.

The example robotic arm controller 4106 includes one or more instructions stored in a memory 4120 that are executable by a robotic processor 4122. The instructions may be configured into one or more software programs, algorithms, and/or routines. The memory 4120 may include any type of volatile or non-volatile memory. The example robotic processor 4122 is communicatively coupled to the navigation computer system 302 and is configured to receive one or more messages related to operation of the robotic arm 210 and/or the coupling plate 504. The example robotic processor 4120 is also configured to transmit to the navigation computer system 302 one or more messages that are indicative of angular positions and/or speeds of joints R1 to R9. The one or more messages may also be indicative that a joint has reached a travel-stop or is being prevented from moving.

The example processor 4120 is configured to determine which joints R1 to R9 are powered in a coordinated manner such that a totality of all motions of all the joints result in the desired image motion at the stereoscopic camera 130. In a "move the camera left" example, there may be complex motions of several joints that cause the camera's surgical image to appear to simply and smoothly translate to the left, from a relative viewpoint of an operator. It should be noted that in the "move the camera left" example, depending on how the stereoscopic camera 130 is connected to the robotic arm 210 through the coupling plate 504, the control signals to specific joints may be drastically different depending on the position/orientation.

The memory 4120 may include one or more instructions that specify how joints R1 to R9 are moved based on a known angular position of the joints. The robotic arm controller 4106 is configured to execute the one or more instructions to determine how instructed camera movement is translated into joint movement. In an example, the robotic arm controller 4106 may receive messages from the navigation computer system 302 indicative that the stereoscopic camera 130 is to move downward along a z-axis and move sideward in an x-y plane. In other words, the navigation computer system 302 transmits indicative of inputs received via the input devices 1410 (translated based on the above-described transformations) regarding desired movement of the stereoscopic camera 130. The example robotic arm controller 4106 is configured to translate the vectors of movement in 3-dimensional coordinates into joint angular position movement information that achieves the desired position/orientation. After any boundary checks are performed, the robotic arm controller 4106 uses the movement delta and the current position/orientation of each of joints R1 to R9 to determine an optimal or near optimal movement sequence for rotating one or more of the joints to cause the robotic arm 210 to move the stereoscopic camera 130 into the specified location. The robotic arm controller 4106 may use, for example, an optimization routine that determines a minimal amount of joint movement needed to satisfy the movement delta vector. After the amount of joint movement is determined, the example robotic arm controller 4106 is configured to send one or more messages (indicative of an amount of rotation and speed of rotation, taking into account any scale factors) to a motor controller 4124. The robotic arm controller 4106 may transmit a sequence of messages to cause the robotic arm 210 and/or coupling plate 504 to move in a defined or coordinated sequence. The sequence of messages may also cause a change in joint speed as, for example, the robotic arm 210 approaches a virtual or physical boundary. The example motor controller 4124 is configured to translate or covert the received messages into analog signals, such as pulse-width modulated ("PWM") signals that cause one or more of joints R1 to R9 to rotate. In some embodiments, the robotic arm controller 4106 in combination with the motor controller 4124 are configured to receive or read joint sensor angular position information (e.g., pose data) and determine, through kinematics, the location and orientation of the robotic joints and stereoscopic camera 130.

The robotic arm controller 4106 receives movement instructions from the navigation computer system 302 and determines, through Jacobian, forward, and/or inverse kinematics, which motors and joints should be activated, how fast and how far, and in what direction. The robotic arm controller 4106 then sends the appropriate command signals to motor power amplifiers in the motor controller 4124 to drive the joint motors in the robotic arm 210.

In the illustrated embodiment of FIG. 12, the example stereoscopic camera 130, the navigation computer system 302, the coupling plate 504, the robotic arm 210, the robotic arm controller 4106, and/or the input devices 1410 receive power via an input power module 4140. The example input power module 4140 includes a power supply (such as power from a wall outlet) and/or an isolation transformer to prevent powerline anomalies from disrupting system performance. In some instances, the power supply can include a battery power supply.

In some embodiments, the navigation computer system 302 operates in connection with the robotic arm controller 4106 to adjust one or more lenses of the camera based on or in cooperation with movement of the robotic arm 210 and/or the coupling plate 504. For example, if the robotic arm 210 is moved toward a surgical site, the navigation computer system 302 operates in connection with the robotic arm controller 4106 to change a working distance or focal point by moving one or more of the lenses of the stereoscopic camera 130 to maintain focus. The navigation computer system 302 operates in connection with the robotic arm controller 4106 to determine, for example, that movement of the robotic arm 210 causes a working distance to decrease. The navigation computer system 302 operates in connection with the robotic arm controller 4106 to determine a new position for the lenses based on the new working distance set by moving the robotic arm 210. This may include moving one or more lenses for adjusting focus. In some embodiments, the navigation computer system 302 may instruct the stereoscopic camera 130 to operate a calibration routine for the new position of the robotic arm 210 to eliminate, for example, spurious parallax.

Integrated Surgical Navigation and Visualization Embodiments

In some embodiments, the above described surgical navigation system (e.g., navigation computer system 302) may be integrated with the surgical visualization system (e.g., stereoscopic camera 130). For example, one embodiment includes a single medical device providing the multiple above described functions of a surgical navigation device and of a versatile digital surgical microscope. The use of the single medical device helps to reduce operating room (OR) footprint. This reduction is important in most operating rooms, which are already crowded due to the many medical devices required for most surgeries.

Figure 15:
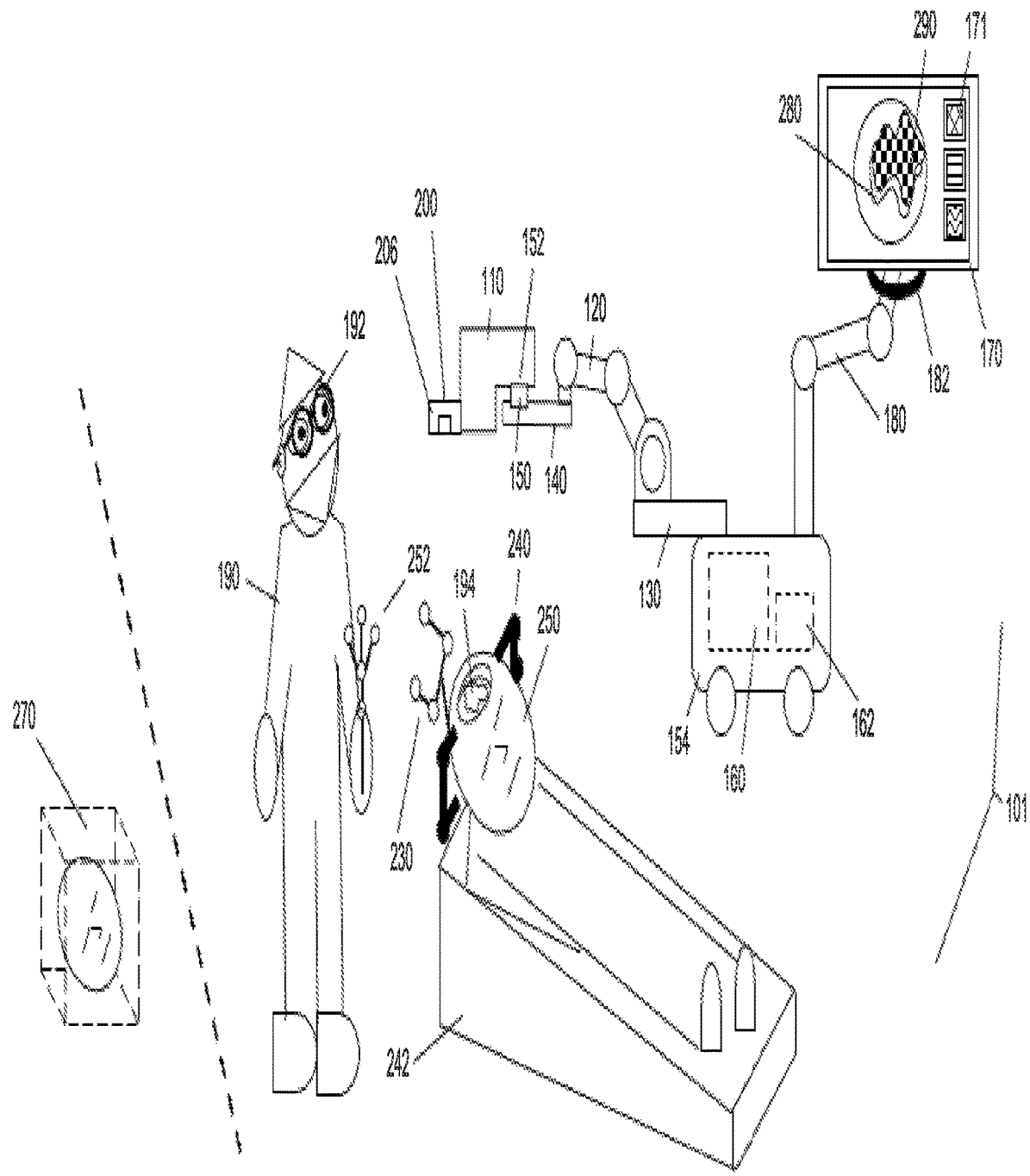
FIG. 15 is a diagram showing an example surgical environment of the integrated surgical navigation and visualization system for automated touchless patient registration, according to an example embodiment of the present disclosure.

FIG. 15 is a diagram showing an example surgical environment of the integrated surgical navigation and visualization system for automated touchless patient registration, according to an example embodiment of the present disclosure. As shown in FIG. 15, the integrated surgical navigation and visualization system 101 may include a digital surgical microscope (DSM) head 110 mounted on a robotic arm 120. To enhance robotic arm reach, the robotic arm 120 may be mounted on an extension platform ("diving board") 131. To extend the range of orientations in which the integrated surgical navigation and visualization system can be used, the DSM head 110 can be mounted on a "universal" coupler 140, which may provide one or more additional degrees of freedom beyond the end of the robotic arm.

In some embodiments of the present disclosure, a force-torque sensor 150 may be incorporated into the robotic arm-DSM head combination (e.g., of the integrated surgical navigation and visualization system 101C). The force-torque sensor 150 may allow users to pose the DSM head at will using physical actions (e.g., as legacy microscopes). For example, the user can physically grab some part or parts of the DSM head and handles attached or otherwise coupled to the robotic arm, and can direct the head toward the desired pose. The force-torque sensor 150 can detect the physical input. A software control module can convert the force-torque sensor's output into an intended change in pose. The same or an additional control module can convert such user intent into a set of robot pose changes that can be streamed to the robot to effect the changes.

The integrated surgical navigation and visualization system 101 may further include a cart 154. The cart 154 can provide a support structure for the robotic arm and diving board. Furthermore, the cart 154 may include an embedded processing unit (EPU) 160 and power management unit with uninterruptible power supply (PMU/UPS) 162. The EPU 160 can communicate with the DSM head, sending commands and receiving command responses and image and status data. The PMU/UPS 162 can manage power for the system 101. The uninterruptible power supply (UPS) 162 can provide the user with the option to unplug the cart for a short time to reposition if needed. The PMU/UPS 162 can also provide the surgeon with an option to have a short time to transition to backup equipment should the hospital power fail.

Imagery can be captured by the digital surgical microscope's optics and image sensor electronics (not shown), sent to the EPU, processed and sent to the three-dimensional (3D) stereoscopic display 170. The 3D stereoscopic display 170 may be mounted on an articulated display mounting arm 180, and its pose may be controlled by display pose adjustment handle 182 e.g., to allow the user to pose the display for optimal viewing quality and comfort.

The surgeon 190 may wear 3D glasses 192 to view the 3D stereoscopic display. The 3D glasses 192 may provide the surgeon to view a 3D stereoscopic view of surgical site 194. Zoom and focus optics in the digital surgical microscope can be controlled by the user, and can provide 3D stereoscopic focused views of the surgical site over a range of working distances (e.g., 200 millimeters (mm)-450 mm) and magnifications (e.g., 3×-11×). In some embodiments the 3D glasses are passive wherein the polarizing film on each respective lens of the glasses left and right are respective conjugates to polarizing film applied to every other line on the display (e.g. the left glasses lens passes the even-numbered lines of the display and block the odd-numbered lines, and vice-versa). In some embodiments, the 3D glasses are active shutter types synchronized to the display such that the left eye passes e.g. every other time-sequential frame shown on the display and blocks the remainder and the right eye performs the complement. In some embodiments, the 3D display may be "glasses-free" and may provide 3D display to the user without need for 3D glasses.

As used herein, "working distance" and "focus" may be used interchangeably. Furthermore, the user interface of the integrated system 101C may refer to working distance as the variable parameter. When a change is made to the desired working distance, the optics move such that the focus distance changes. Thus, the distance between the microscope and the focus surface may change, and that distance can be generally considered to be the working distance.

The integrated surgical navigation and visualization system 101C and/or the legacy surgical navigation system 101A may include a navigation camera ("navigation localizer" or "localizer") 200. For example, in the legacy surgical navigation system 101A shown in FIG. 1A, the navigation localizer 200 may be mounted on the articulated localizer mounting arm 202. The navigation localizer 200 may be user-poseable by localizer pose adjustment handle 204.

A navigation-trackable patient reference target 230 can be mounted rigidly to a patient clamp (e.g. a "Mayfield" clamp) 240. The patient clamp 240 may be mounted near surgical bed 242 where the patient 250 resides. The patient clamp 240 may avoid areas of the patient's anatomy to move in relation to the patient reference array.

The digital surgical microscope may be rendered to be compatible with (e.g., by being rendered trackable by) the localizer with the addition of the DSM navigation target (e.g., "shellmet," as derived from "shell" and "helmet.") 210. Various styles of navigation targets can be used with the system such as the retro-reflective spheres shown schematically in the Figure or image-based corner targets described elsewhere in this document.

The localizer may detect the pose in some reference frame of compatible devices (i.e. trackable devices, navigation targets) in its viewing space. The localizer may supply this information to the EPU responsive to requests for such information in a quasi-real-time fashion (e.g., 15 times per second in a "polling" method) or at a constant rate even without requires (a "broadcast" method). Typically, the reference frame in which the poses are reported may be that of the localizer. In some implementations, however, precalculations may be performed in order to report the poses from a different reference frame.

Relevant rigid patient anatomy such as the skull may be mounted to or accessible via, clamp 240. Systems and methods described herein may guide the user through a patient anatomy registration procedure, as part of the preparation workflow. This registration procedure can determine the pose of the patient data 270 relative to the navigation target affixed rigidly either directly or indirectly to the relevant patient anatomy.

In some aspects, the integrated surgical navigation and visualization system 101 may comprise a navigation system integrated into the DSM head 102, which may be mounted on robotic arm 120. The cart 154 may support the robotic arm 120 as well as a boom-mounted 3D stereoscopic display (e.g., 3D stereoscopic display 169) and a mast-mounted touchscreen 171 for user input. Additional displays can also be connected optionally.

The integrated surgical navigation and visualization system 101 may provide 6 degree of freedom (6DoF) position and orientation information of the head relative to some reference or target viewable by the navigation device in the scene. The digital surgical microscope may provide stereoscopic visualization over a range of magnifications (typically 1×-9×) and a range of working distances (typically 200 mm-450 mm.)

An objective of surgical navigation may include guiding the surgeon around the patient's anatomy during a surgical procedure so that the surgeon can complete the procedure in the most effective, least damaging way. The patient's anatomy has typically been scanned in a device such as a computed tomography (CT) machine or a magnetic resonance imaging (MRI) machine, and the results may be stored in a format such as a stack of image "slices" of the anatomy from which the 3D anatomy can be reconstructed and explored. The above described objective can thus achieved by providing a view or views of various levels of relative position and orientation information between the patient data and various objects such as a navigation probe and/or the digital surgical microscope's optical axis.

Figure 16:
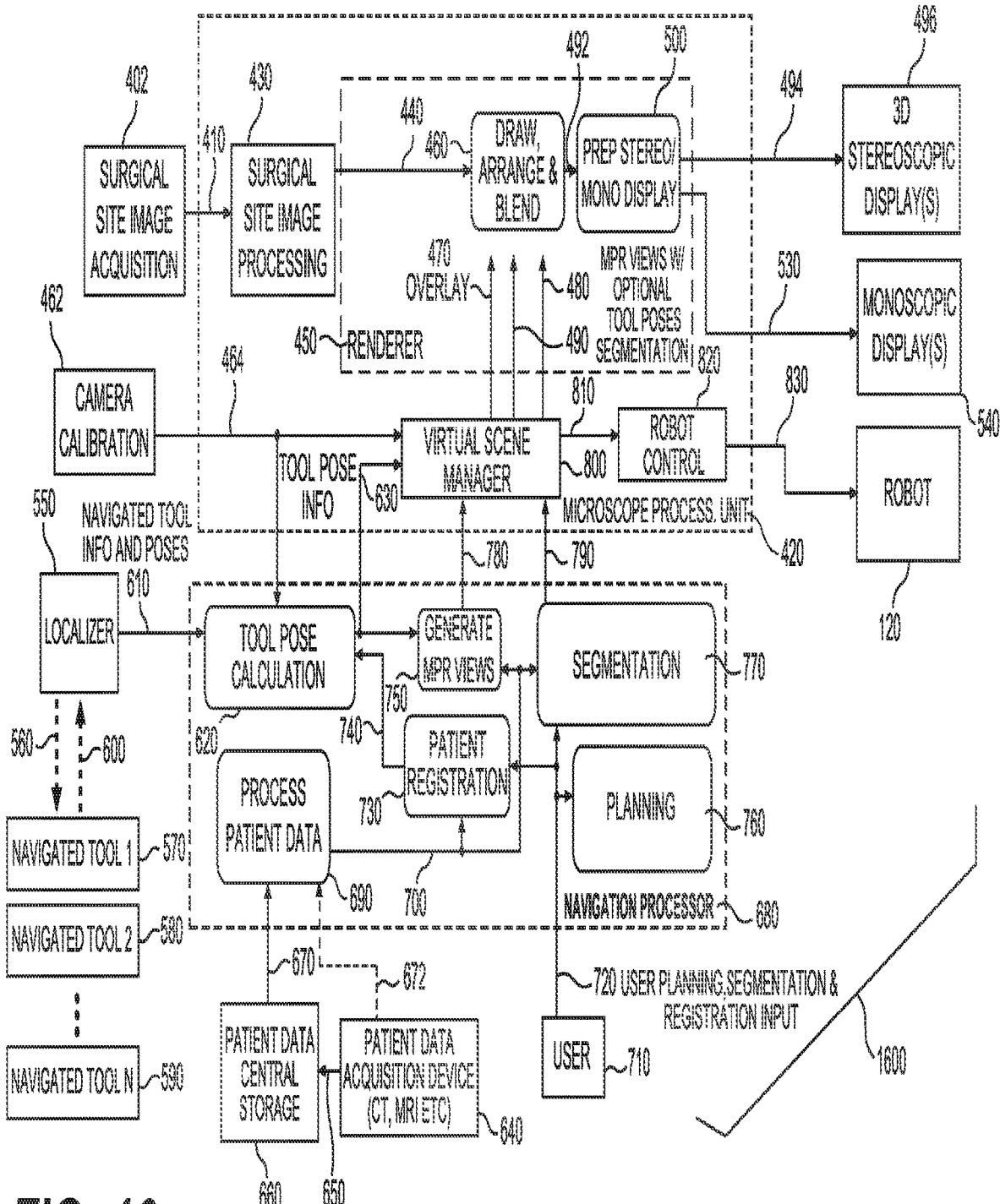
FIG. 16 is a flow diagram showing an example pipeline for the integrated surgical navigation and visualization system, according to an example embodiment of the present disclosure.

FIG. 16 is a flow diagram showing an example pipeline 1600 for the integrated surgical navigation and visualization system, according to an example embodiment of the present disclosure. Furthermore, pipeline 1600 describes one or more examples of how surgical visualization and navigation information is generated, captured, processed and displayed in the integrated surgical navigation and visualization system 101. It is understood that while the processes associated with pipeline 1600 are shown as near-linear, one or more processes can happen concurrently and/or in a different order than is presented here.

Pipeline 1600 may begin with image acquisition of a surgical site (block 402) (e.g., as part of an image data stream). The surgical site image acquisition may occur at or be performed by a surgical site image acquisition module. An example image acquisition module of a fully featured stereoscopic digital surgical microscope, including light source(s), zoom and focus optics, image sensors and all supporting electronics, software, firmware and hardware, is further described in U.S. Pat. Nos. 10,299,880 and 10,334,225, the entireties of which are hereby incorporated by reference herein. This image acquisition module may generate surgical site image data stream 410, which may be communicated to microscope processing unit 420 and the associated surgical site image processing module 430. Images may be captured and processed at a frame rate high enough to be perceived as video by the user, for example, 60 frames per second (fps.). Thus, images may be considered to be "image data stream." It is to be understood that, where a two-camera stereoscopic digital surgical microscope is described, the concept may be extendible to an N-camera digital surgical microscope where N is 2 or greater.

The surgical site image processor may process the image data 410 received from the surgical site image acquisition module, and may produce processed image data stream 440. The processed image data stream 440 may be sent to the renderer module 450, and more specifically to the draw, arrange & blend module 460. The renderer module 450 may also receive camera calibration information 464, which may be generated in an offline process. Methods and systems for producing camera calibration information are further described in U.S. Pat. Nos. 9,552,660 and 10,019,819, the entireties of which are hereby incorporated by reference herein. Camera calibration information may be generated for each "eye" of the stereoscopic digital surgical microscope. The camera calibration may provide the renderer module with the option to set up its virtual cameras such that, along with proper navigation data to be described, rendered overlay objects appear in similar perspective, size (magnification) and pose as objects captured by the surgical site image acquisition module. For example, the rendered overlay of a portion of a patient's skull and skin may appear in a similar perspective and pose as a live view of the same portion through the digital surgical microscope.

Such combination may continue in the draw, arrange & blend module 460, where surgical site processed image data stream 440 may be combined with patient data overlay 470, multiplanar reconstruction (MPR) views with optional tool poses 480, and segmentation information 490 into a raw stereoscopic rendered image stream 492. The raw stereoscopic rendered image stream 492 may be sent to the stereoscopic/monoscopic display preparation module 500. The stereoscopic/monoscopic display preparation module 500 may transform the raw stereoscopic rendered image stream 492, as necessary, into the final stereoscopic display output data stream 494 required by the stereoscopic display(s) 496. Different stereoscopic displays may require different final stereoscopic data formats, which the display preparation module may provide. Also or alternatively, there may be one or more monoscopic displays 540. The various data formats 530 associated with the monoscopic displays 540 may also be provided via configuration by the display preparation module.

The preceding few paragraphs discuss the acquisition of a live surgical site image stream, its processing and combination with navigation module output and the display thereof. The navigation module output is formed as follows.

The localizer 105 may comprise a sensing device having a certain scene visible to its field of view. The scene may depend on the design of the device and pose of the device. In some embodiments, the localizer 105 may send a communicative query 560 to one or more navigated tools. The navigated tools, which might be present in the scene, may include, for example, a first navigated tool 570, a second navigated tool 580, and/or up to a certain number of such tools 590. Such a communicative query in some embodiments may involve directing infrared light either at a constant level or in a known pulse rate and/or sequence toward the scene. In some other embodiments, the query may be of a passive nature, such as relying on ambient visible light to illuminate a high-contrast pattern formed on the navigated target(s). Control of this infrared light (e.g., by switching on and off, or by selecting a specific wavelength) may help avoid illumination interference with the digital surgical microscope fluorescence capabilities.

The communicative query may be sent back as a response 600 from each respective navigated tool. The response may be received by the localizer, and may be sent as tool information and pose information 610 for each navigated tool. The localizer may run these query and/or responses as send/receive cycles at real-time or near real-time rates such as 15 Hertz (Hz) to 30 Hz. The pose information for each tool may be determined in a common space for all tools. For example, a coordinate reference frame origin and orientation relative to a rigid feature of the localizer may be the common space that is used. The tool and pose information 630 may be received by tool pose calculation module 620.

In an offline process, a patient data acquisition device (CT, MRI, etc.) 640 may be used to scan the relevant anatomy of patient 250 to generate acquired or received patient data 650. The acquired or received patient data may be optionally stored in a patient data central storage 660. The patient data may be sent (e.g., from the central storage 670) to the navigation processor 680. Alternatively, the patient data may be sent to said processor as patient data 672 directly from acquisition device 640.

It is understood that the physical location of each navigation processor, the microscope processing unit and all other main components may vary with implementation. Generally, the microscope processing unit 420 and the navigation processor 680 may reside in the embedded processing unit 160, but this is not a requirement. For example, the navigation processor might be physically located inside the same housing as the navigation camera, remote from the cart which might house the embedded processing unit.

The patient data processing module 690 may process the patient data into format(s) needed by various modules in the rest of the system as processed patient data 700.

Figure 18:
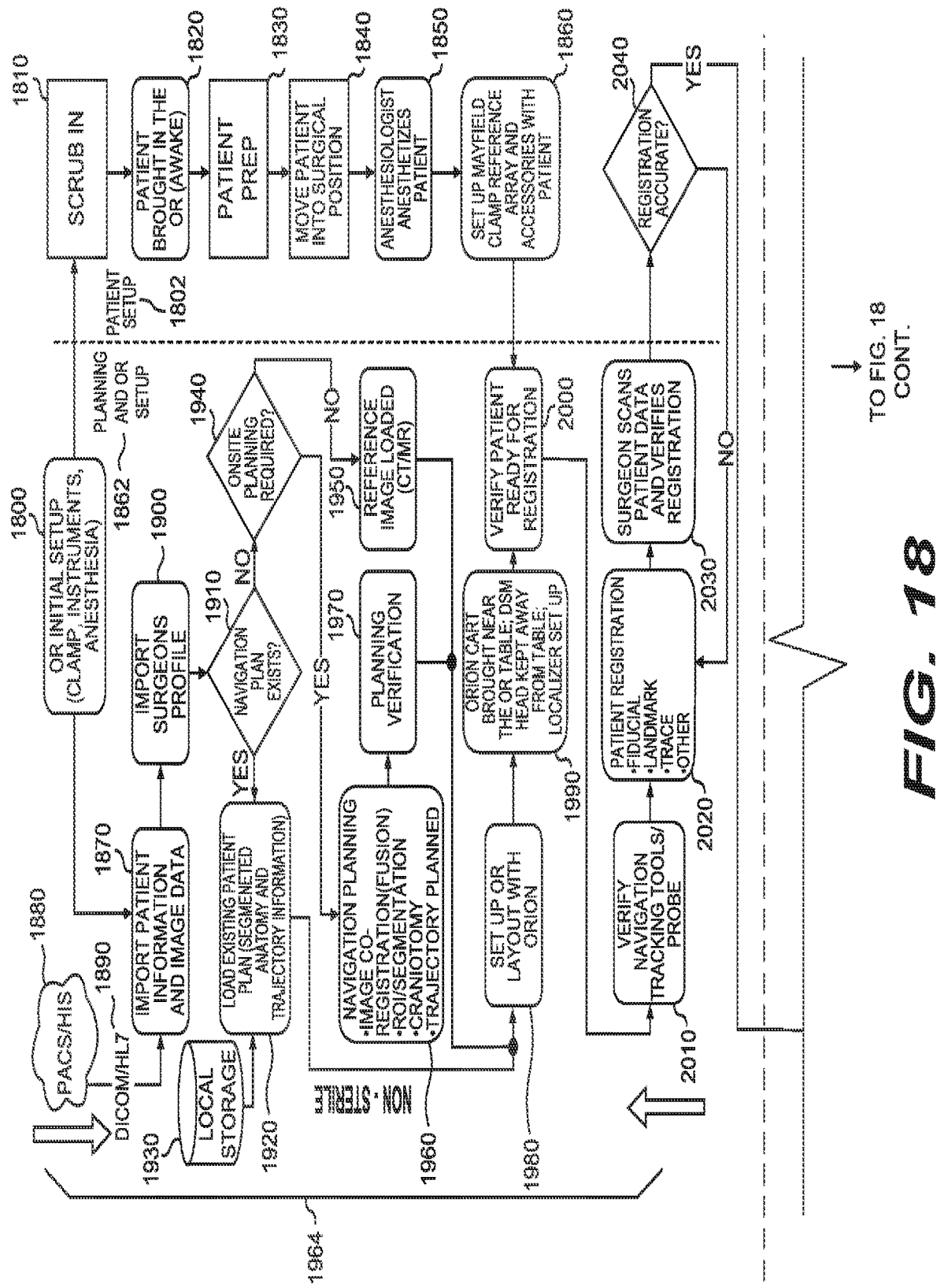
FIG. 18 is a flow diagram showing an example workflow performed for the integrated surgical navigation and visualization system, according to an example embodiment of the present disclosure.
Figure 18:
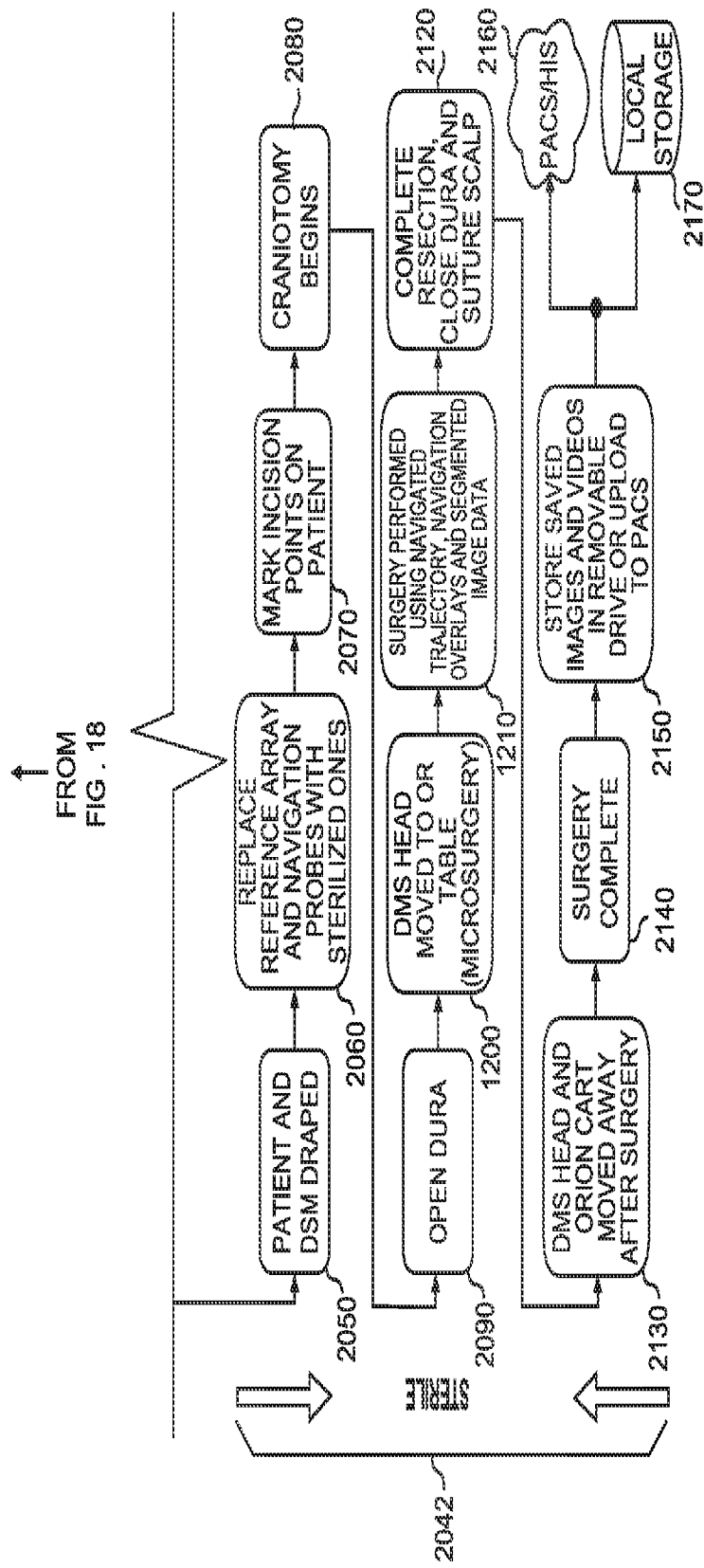

The relative timing of processes associated with this pipeline is further described in relation to FIG. 18. As will be described below, the user 710 may direct the software via user planning, segmentation and registration input 720 to perform those respective workflow steps. The patient registration module 730 may direct the user and accept user input to generate patient registration information 740. The registration information 740 may describe the pose relation between the processed patient data 700 and the patient reference navigation target 230.

Use of the processed patient data 700 may continue as the multiplanar reconstruction view generator 750 generates multiplanar views 780. The multiplanar views 780 may assist the user in the use of the planning module 760 to generate opening, approach and objective patterns and trajectories (as standard features in surgical navigation systems). In some embodiments, a 3D view generator may further assist the user in such endeavors, e.g., by generating a 3D representation of the patient data. The view of the 3D representation can be adjusted based on a desired pose and/or scale.

The multiplanar views 780 and/or any 3D representation of the patient data may assist the user in use of the segmentation module 770 to generate segmented geometry 790. For example, if the patient pathology is a tumor located in some certain location of the patient's brain, the segmentation module 770 provides the user the option to isolate the tumor in the patient data such that the segmented geometry represents the tumor in size, shape and pose.

One or more of the camera calibration information 464, tool pose information 630, multiplanar reconstruction views 780, 3D representation of the patient data, and segmented geometry 790 may be provided to the virtual scene manager 800. The virtual scene manager 800 may generate representations of the patient data overlay 470, multiplanar reconstruction views with optional tool poses 480, and segmentation information 490 usable by the draw, arrange & blend module 460 in various ways, as configured by the user.

For example, the overlay may be displayed at a distance along the optical axis of the digital surgical microscope, with an on/off option available. Also or alternatively, said distance along the optical axis is may be controllable by the user, allowing an "X-ray vision" of patient data beneath some portion of the patient anatomy.

In existing conventional systems, where the overlay is injected into traditional optical microscopes, the focal plane of the overlay display is distinctly one single plane whereas the view of the scene is an analog collection of many focal distances. In such conventional systems, users are often forced to refocus their eyes when switching between viewing the live surgical site and viewing the overlay. Further the perceived location of that one single overlay display plane is often located significantly away from the general surgical site scene, for example a few centimeters above the site. However, systems and methods described herein may allow the overlay information to be presented on the same display focal plane as the stereoscopic view of the live surgical site.

While there may be a single display focal plane of the stereoscopic view of the live surgical site (e.g., the plane of the stereoscopic display), the user may still perceive a full or perceptually full analog collection of many focal distances owing to the wonders of the human visual system.

Further to the example, one or more (or all) of the three multiplanar reconstruction views plus a 3D representation may optionally be displayed at the side of the main display screen, thereby integrating, in one display, the live surgical view along with the navigation information. This integration is yet another benefit over existing multi-device systems, which often force the user to look back and forth between the visualization system and the navigation system, mentally carrying a large informational load between the systems.

Figure 17:
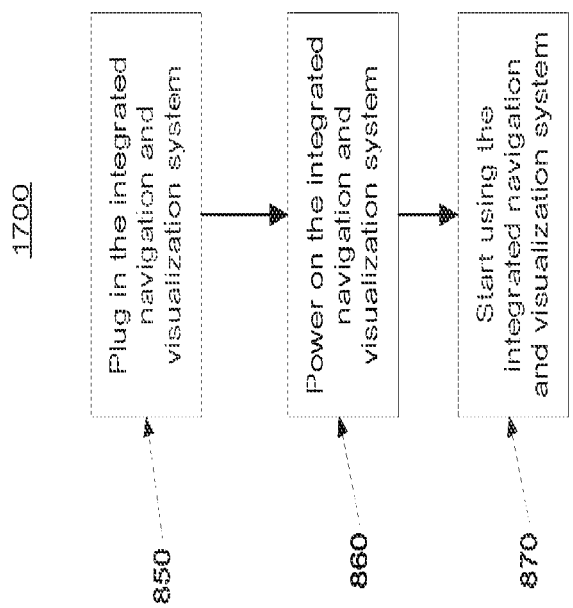
FIG. 17 is a flow diagram showing an example process for starting up the integrated navigation and visualization system, according to an example embodiment of the present disclosure.

FIG. 17 is a flow diagram showing an example process 1700 for starting up the integrated navigation and visualization system, according to an example embodiment of the present disclosure. For example, the user of the integrated navigation and visualization system may be trained to follow system preparation steps as shown in process 1700. At step 850, the user may plug the integrated navigation and visualization system into the hospital main power (e.g., by plugging into a wall socket). At step 860, the user may power the system on (e.g., by turning the "on" switch). At step 870 the user may begin using the system. Workflow steps after turning on the system are further described below, in relation to FIG. 18.

The relative ease of starting up the integrated navigation and visualization system, as illustrated in FIG. 17, confers a major advantage of the integrated surgical navigation and visualization system over conventional multi-component systems for navigation and visualization, as the integrated surgical navigation and visualization system eliminates or obviates the need to perform various setup steps or startup processes. For example, as shown in FIG. 17, a single power plug may be required to be connected to hospital mains, whereas conventional multi-component systems may typically require at least two such connections. Furthermore, physical connections need not be made by the user between the navigation system and the visualization system. In contrast, conventional, multi-component systems may typically require some form of connectivity between the separate navigation system and visualization system. Furthermore, workflow synchronization need not be made between the navigation system and the visualization system. In contrast, conventional, multi-component systems may require some form of such workflow synchronization.

FIG. 18 is a flow diagram showing an example workflow performed for the integrated surgical navigation and visualization system, according to an example embodiment of the present disclosure. A software application on the integrated surgical navigation and visualization system may perform software portions of the pipeline and may provide a workflow for the user to follow. Various portions of the workflow may be implemented in a workflow command and control module while other portions may be performed outside of the software and outside of the system. Such portions may be presented in order to provide a full picture of system usage.

For clarity, workflow command and control module is not shown in the data acquisition, processing and display pipeline 1600. The implemented workflow is described herein. It is understood that while this workflow is described in a near-linear fashion, some processes can happen concurrently and/or in a different order than is presented here.

The workflow may begin with a set up of the operating room ("operating room setup") 1800, where equipment, tools and accessories may be brought into the operating room. Such equipment, tools, and accessories may include, but are not limited to, the integrated surgical navigation and visualization system, patient clamp(s), navigation tools, surgical instruments, and anesthesia equipment. A group of workflow steps considered as the patient setup workflow steps 1802 may be undertaken by operating room staff. These steps may begin with a scrub in 1810, where staff who enter the sterile field perform their pre-cleaning and entry into sterile clothing. Additionally some preliminary patient scrub may be performed at this time.

At step 1820, the patient may be brought into operating room awake. Afterwards, step 1830 may include patient preparation 1830, which may involve include hair removal near the surgical site and further sterilization of the nearby area. At step 1840, the patient may be moved into a surgical position and at step 1850, the anesthesiologist may anesthetize the patient.

Portions of the navigation setup associated with the patient may be performed in step 1860. In some aspects, the relevant anatomy of the patient may be fixed rigidly relative to the navigation reference target. In neurosurgery, for example, the patient's skull may be fixed rigidly into a Mayfield clamp and the navigation reference target fixed rigidly to the clamp. Accessories, such as a navigated probe, may be made available at this time, for example, by removing them from their sterilization kit and placing them on a sterile table to be available for the surgeon.

The workflow may progress to a set of steps referred to herein as planning and operating room setup 1862. Of the steps associated with planning and operating room setup 1862, a steps 1864 may typically occur in the non-sterile realm of the operating room, e.g., with equipment that is not required to be sterilized.

The user may proceed to use the software application on the integrated surgical navigation and visualization system to import patient information and patient image data at step 970 from patient data central storage. In some aspects, the patient data central storage may comprise one or more of a picture archiving and communication system (PACS), a hospital information system (HIS), or a radiology information system (RIS), collectively referred to as PACS/HIS/RIS 1880. The patient information and patient image data may be provided over a communications interface such as hospital ethernet as formatted patient data 1890. The patient information and/or patient image data may be formatted using one or more options (e.g., Digital Imaging Communication in Medicine (DICOM), Health Level (HL7), etc.).

At step 1900, the surgeon profile may be imported. Alternatively, a surgeon profile may be created, e.g., if none exists. At decision step 1910, if a navigation plan exists, then at step 1920 the user may load existing patient plan (segmented anatomy and trajectory information) from local storage 1930. However, if no navigation plan exists, the user may determine whether onsite planning is required at decision step 1940. If a navigation plan does not exist and/or if no onsite planning is otherwise required, then a reference image may be loaded at step 1950. If navigation planning is required or desired, then at step 1960 navigation planning may be performed. Additional steps for navigation planning may include, for example, image modality co-registration or fusion (e.g., for registering MRI to CT), region of interest (ROI) specification, segmentation of one or more regions, craniotomy (in the case of cranial neurosurgery) or other approach specification, and trajectory planning. At step 1970 the navigation planning may be verified, e.g., by the lead surgeon.

At step 1980, the operating room layout may be determined. The operating room layout may involve a positioning and/or an orientation of the integrated surgical and navigation visualization system, and how various pieces of operating room equipment are to be posed at various phases during the procedure.

At step 1990, the integrated surgical navigation and visualization system may be brought near an operating room table where the patient resides. The digital surgical microscope head may be kept away from sterile field for now. The localizer may be posed such that it can "see" (e.g., receive within its field of view), the relevant navigated tools needed during the current workflow steps. For example, during registration, the localizer may need to see the navigated hand probe and the navigated patient reference target.

At step 2000, the user may verify that the patient is ready for registration. At step 2010, the user may verify that the localizer is tracking the tools needed for registration. In some embodiments, these tools may include the navigated hand probe and the tracking may involve locating the navigated patient reference target. In other embodiments, the tracking may involve locating the navigated target(s) on the digital surgical microscope and the navigated patient reference target.

At step 2020, a patient registration may be performed. Various forms of registration may be available in the surgical navigation visualization system. A chosen registration may be a function of several variables, including but not limited to a type of procedure, patient position, and/or a patient condition. Forms of patient registration available may include, for example, fiducial matching, landmark matching, and trace.

In fiducial matching, fiducials may be added to the patient (e.g. by affixing) before the volume scan (e.g., via CT or MRI) is performed. The fiducials may be kept on the patient. The locations of the live physical fiducials may then be matched with those in the volume scan. The specification of the locations of the fiducials on the live patient may be performed using the tip of the navigated probe in some embodiments, and the focal point of the digital surgical microscope in other embodiments.

In landmark matching, physical landmarks on the live patient (e.g., the corners of the eyes) can be matched to corresponding landmarks in the volume scan data. Similar to fiducial location, the specification of the locations of the landmarks on the live patient may be performed using the tip of the navigated probe in some embodiments, and the focal point of the digital surgical microscope in other embodiments.

In trace, the user may be instructed by the software to use the navigated probe to trace over a uniquely shaped portion of the user anatomy (e.g., the saddle of the bridge of the nose including some of the area under the eyes). Also or alternatively, the focal point of the digital surgical microscope may be used in conjunction with robot moves about the region, with an autofocus mechanism providing a means of staying on the surface of the patient's anatomy.

Other forms of patient registration may include touchless registration using a laser, and touchless registration using photogrammetry/stereogrammetry.

At step 2030, the surgeon may review patient data and may verify the registration. If the registration is not accurate enough (e.g., does not satisfy a similarity threshold), decision step 2040 provides a logic for returning to step 2020 to repeat the registration step(s). If or after the registration is sufficiently accurate (e.g., satisfies a similarity threshold), workflow proceeds to steps 2042, which occur in most instances in the sterile realm of the operating room.

To prepare the patient and the digital surgical microscope for use in the sterile field, step 2050 includes covering the patient and the digital surgical microscope in one or more sterile drapes. Appropriate openings may be aligned as needed for the digital surgical microscope. For example a lens window may be aligned to the optics main entrance to the digital surgical microscope. The area of the patient where surgical entry is to occur may be exposed through the patient drape. The patient's skin may be sterilized with an antiseptic solution.

The earlier patient registration previously described in step 2020 may have occurred in a non-sterile field with an undraped patient and clamp as well as possibly a non-sterile navigated probe. Since the clamp was undraped and non-sterile, the patient reference navigated target may considered non-sterile. Thus, at step 2060, this target and/or the navigated probe (e.g., if used) may be replaced with sterile equivalents.

Referring to the workflow of FIG. 18, in relation to steps after 2060, the main portion of the surgery may begin. At step 2070, using the planning, incision points and/or paths may be marked or otherwise indicated on the patient. An advantage of the integrated surgical navigation and visualization system is that these incision points and/or paths can be drawn virtually as overlays over the live view as an alternative to physically marking the patient. This is quite useful since such points and/or paths may persist throughout the approach whereas physical marks are immediately removed since they are on the outermost layer of the skin which is the first to be peeled back or otherwise moved out of position (and out of visibility) during an approach.

The opening and approach may commence at step 2080 with patient incision. Some of the steps in this workflow may be specific to cranial neurosurgery but may apply to many common surgeries. At step 2080, the craniotomy begins. Another advantage of the integrated surgical navigation and visualization system may include the ability to plan the craniotomy shape in advance and draw it virtually as an overlay over the live image such that the surgeon merely needs to "cut by numbers" and follow the path with the cutting tool as drawn onscreen. This overlay persists optionally under control of the user during the whole time of the approach.

At step 2090 (e.g., as part of cranial neurosurgery) the dura may be opened. At step 2100, the digital surgical microscope head may be moved to where surgical site on patient resides. In some aspects, this step can occur earlier in the workflow shown in FIG. 18, e.g., to provide the virtual overlays for the skin incision and craniotomy steps.

At step 2110, the bulk of the surgery may be performed. More advantages of the integrated surgical system become apparent. For example, the planned trajectory may be drawn on the multiplanar reconstruction views responsive to user request. The robotic arm can be commanded under the user request to move the optical axis of the digital surgical microscope to align with the pre-planned trajectory. Also or alternatively, such alignment may be used to align the optical axis of the digital surgical microscope quasi-continuously in quasi-real-time to some vector such as the axis of a NICO port of the axis of a spinal dilator tool. Thus, the surgeon may be freed from having to manually position the microscope to keep a useful view down such axes which can change poses throughout the procedure.

Also or alternatively, at step 2110, navigated overlays may be used to allow the surgeons to "know where they are" within the patient anatomy. Furthermore, the navigated overlays may be used to allow the surgeons to have "X-ray vision" by drawing from the patient volume data portions of the patient anatomy, which might remain beneath physical structures on the patient which have not yet been removed.

When segmentation is used for example to specify the 3D shape and pose of a tumor, such a 3D shape may be drawn under user control in the correct perspective, pose, and scale to within some accuracy, and may be blended with the live image stream. This specification may allow the surgeon to identify which parts of not-yet-resected tissue might be "tumor" or "not tumor."

After the main part of the surgery (for example a tumor resection or aneurysm clamp) is complete, the dura maybe closed and the scalp may be sutured in step 2120. The digital surgical microscope head and cart may be moved away at step 2130. The surgery may be complete at step 2140.

At step 2150, images and/or video recorded during surgery may be stored (e.g., locally, at picture archiving and communication system (PACS) 2160, at a local storage 2170 for images and/or video recorded during surgery).

Figure 19:
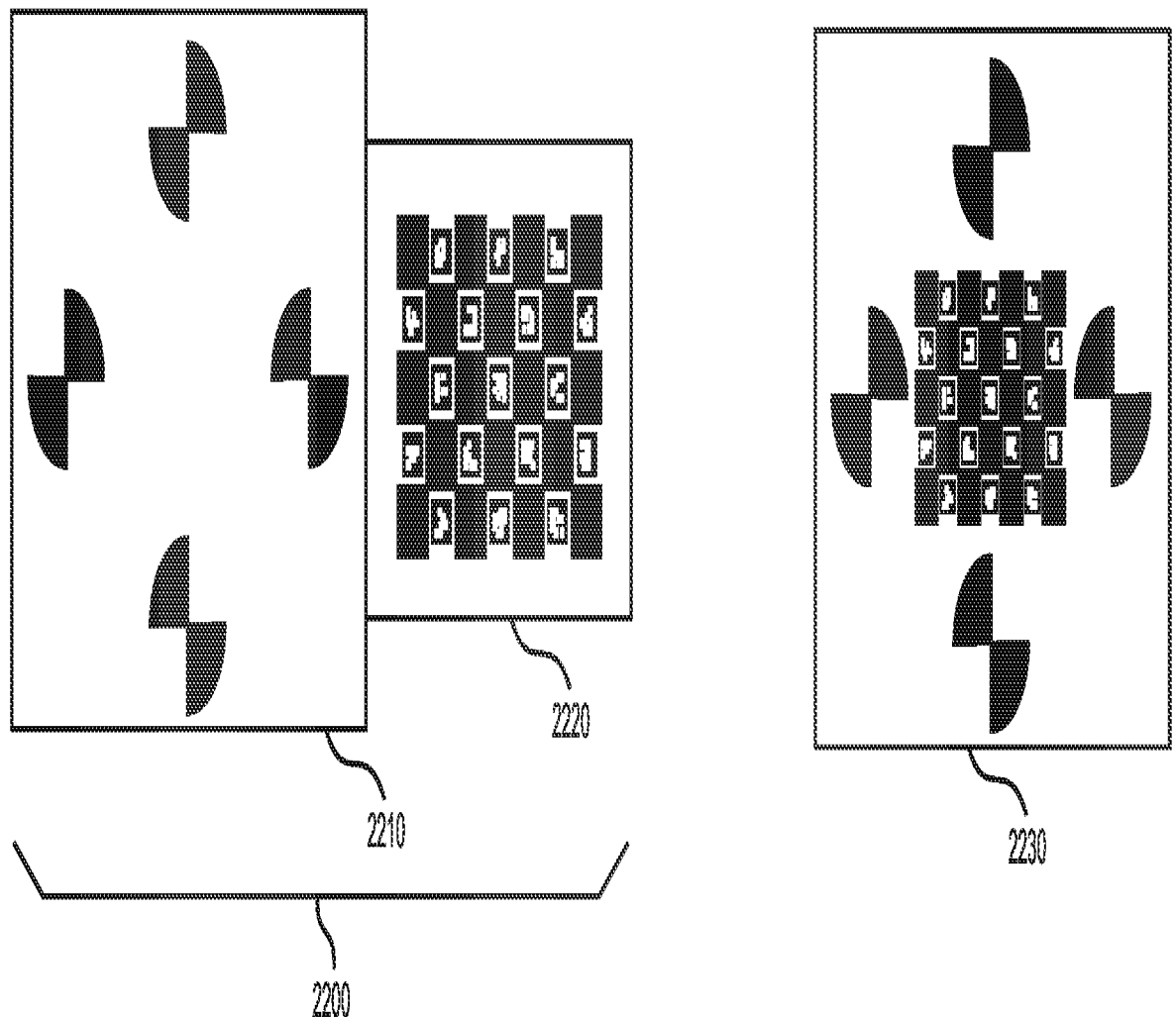
FIG. 19 is a diagram illustrating a calibration object applicable to the integrated surgical navigation and visualization system, according to an example embodiment of the present disclosure.

FIG. 19 is a diagram illustrating a calibration object applicable to the integrated surgical navigation and visualization system, according to an example embodiment of the present disclosure.

Using standard camera calibration methods, such as OpenCV cv:calibrateCamera, the following intrinsic camera parameters may be determined for each of the two camera eyes of the stereoscopic digital surgical microscope: principal point (cx, cy); and focal distance (fx, fy).

The cv:calibrateCamera process may be realized by taking snapshot images of a calibration target at multiple poses of the respective camera eye relative to the target which target contains computer-vision-detectable sub-objects. The sub-objects in some implementations may be unique relative to each other and thus the location of each individual sub-object relative to the whole calibration target may be known.

In some aspects, cv:calibrateCamera may use a simultaneous solving process to determine the intrinsic camera parameters as well as the extrinsic camera parameter at each pose of the camera. Said extrinsic parameters are composed of a three-dimensional translation and a three-dimensional rotation of the respective camera eye relative to a predetermined reference frame of the calibration target:

Tx, Ty, Tz (e.g., translations from the origin along each axis of the calibration reference frame); and Rx, Ry, Rz (e.g., rotations about each axis of the calibration reference frame)

The extrinsic parameters may be unique to each unique pose of the respective camera eye relative to the calibration target reference frame for each such of the multiple poses used to generate snapshot images for use in the calibration process. In contrast, the intrinsic parameters may be constrained to remain constant over all such images.

The concepts may be extensible to N-camera digital surgical microscope where N is 2 or greater.

A navigated calibration object 2200 may be created comprising a navigation target 2210 trackable by the navigation camera 105 as well as computer-vision-detectable sub-objects 2220 arranged in the reference frame of the navigation target in known positions and rotations (i.e. in known poses.)

A navigation target 2210 trackable by the navigation camera may be affixed rigidly to some physical frame common to the cameras' respective optical systems. In some embodiments, one or more additional such targets may be placed variously about the frame such that the localizer (i.e. the navigation camera) can "see" at least one target at any time over a large range of poses of the digital surgical microscope head relative to the localizer.

The navigated calibration object may be placed within view of the stereoscopic digital surgical microscope.

The stereoscopic digital surgical microscope can be set to a given zoom and focus distance. Furthermore, the stereoscopic digital surgical microscope can be made to move through N poses relative to the navigated calibration object, keeping the navigated calibration object in the field of view, and recording an image for each camera eye at each pose.

Disparity in a stereoscopic digital surgical microscope may be defined for a given onscreen point or region as the number of pixels of separation between the left and right camera eyes for a given point, region or feature of the scene at the onscreen point. For example, the center of the screen may be chosen as the point at which disparity is measured, and the onscreen center of the left camera eye may be viewing a scene feature such as the bottom left corner of an irregularly shaped triangle.

It may be determined (e.g., via user input or automatically via computer vision pattern matching such as OpenCV cv:matchTemplateo) that the same feature appears 5 pixels to the right of the onscreen center of the right camera eye. The disparity in this case may be "+5 pixels." The determination of which direction about the central axis of the screen is positive versus negative sign may be arbitrary and predetermined.

The stereoscopic digital surgical microscope can be calibrated such that, across the whole operating range of zoom and working distance, the disparity at the center of the screen for each camera eye is at or near zero pixels when the system is in "generally good focus." In some embodiments, other points on the screen may be used and/or other values of disparity.

During image acquisition at the N poses used in calibration, the view of the navigated calibration object may be optionally kept in generally good focus via robotic movement until an "in-focus" metric is optimized such as minimized disparity. The robotic movement can be controlled via a feedback loop. The feedback loop may continually monitor the measured parameter disparity and may use a measurement to drive the robot arm such that the stereoscopic digital surgical microscope moves closer to or farther from the navigated calibration object along an estimated optical axis of the microscope, thereby adjusting the measured disparity.

The navigation camera 105 (also referred to as "localizer") may continually image the navigated targets (also referred to as "tools") in its view. The navigation processor 680 may subsequently calculate the pose in some reference frame of each such tool, and may report said tool pose info to the embedded processing unit. The reference frame used may be referred to as the "localizer reference frame" and may be typically posed somewhere convenient and sensible on the localizer camera such as at the midpoint of the line joining the camera's two eyes when a stereoscopic localizer camera is used. For example, one axis of the reference frame may be aligned with said line, another axis may point orthogonally outward from the front face of the localizer camera, and a third axis may be oriented to satisfy a right-handed Cartesian coordinate system.

At each pose of the robot (and hence of the stereoscopic digital surgical microscope) where a calibration snapshot image is recorded, the tool pose info for each the navigated calibration object and the navigated target(s) on the digital surgical microscope can also recorded and indexed to the calibration snapshot image for later use.

These poses may be represented as homogeneous transformation matrices, and may be able to transform one reference frame into another. The naming of such matrices may be chosen to allow "chaining" of multiple matrices, where the final result of the multiplication of a succession of matrices may result in the transformation of the rightmost-listed reference frame into the leftmost-listed reference frame, and the inner names must match. This naming and representation allows for rapid on-sight verification, e.g., to ensure that the math is correct.

The transformation from space "B" to space "A" can be written "backwards" as A_T_B and pronounced, "the transformation from space B to space A is A_T_B: B to A."

This naming may allow easy "chaining" of transformations by lining up the "inner" pairs of space names. The final transformation may be the "outer" pair of space names.

EXAMPLE

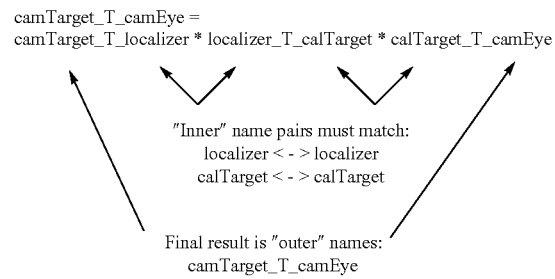

The inverse of a matrix A_T_B can be written as B_T_A. For example: calPattern_T_calRefFrame=calRefFrame_T_calPattern.inverse( ) (1.1)

In camera calibration, the camera may be modeled as a pinhole with a reference frame, the origin of which may be the pinhole. The camera can be placed such that the scene appears on one side of the pinhole and the sensor appears on the other side of the pinhole. For mathematical simplification, the sensor may be moved conceptually to the same side as the scene. The pinhole can be variously referred to as the "eye point", the "camera eye", or the "center of projection."

The pose of the navigated calibration object in the localizer reference frame can be denoted as: localizer_T_calTarget (2.1)

When multiple targets are used on the digital surgical microscope (e.g., to improve visibility over the range of possible camera poses), the poses of the multiple navigated targets on the digital surgical microscope can be reported in the same way as when a single navigated target is used. For example, a single representative pose in the localizer reference frame can be reported as: localizer_T_camTarget (2.2)

This reporting may not necessarily just be a notation convenience. When multiple navigated targets are used on the digital surgical microscope, one target can be chosen as the primary target and the locations of the others can be determined relative to that primary target. Thus, the navigation processor may calculate and report a single such tool pose in the tool pose information stream.

Each snapshot used in the camera calibration process may provide the pose of the camera eye relative to some predetermined reference frame of the calibration object, which typically is part of some calibration pattern used in the calibration object. Thus, the pose (i.e. the extrinsic parameters) of the camera eye can be determined relative to that calibration pattern, and may be denoted as:

calPattern_T_camEye (2.3), where "camEye" denotes the location and orientation (i.e. the "pose") of the reference frame of the center of projection and coordinate system of an idealized pinhole camera model of the entire optical system for a given single camera of the dual-camera stereoscopic digital surgical microscope.

For simplicity, the calibration object reference frame may be taken to be coincident with the reference frame of the navigated target mounted to the calibration object. The pose of the calibration pattern relative to the (reference frame of the) navigated target mounted to the calibration object can thus be denoted as:

calTarget_T_calPattern (2.4)

In some embodiments, this is made to identity by making the reference frame of the calibration pattern be coincident with the reference frame of the navigation target mounted on the calibration object as in 2230.

For a given single calibration image with the associated respective camera eye poses relative to the calibration pattern, the pose of a given camera eye relative to the single representative navigated target on the digital surgical microscope may be calculated as previously described (e.g., inverse notation, matrix "chaining" method, etc.):

$$camTarget\_T\_camEye = camTarget\_T\_localizer*localizer\_T\_calTarget*calTarget\_T\_calPattern*calPattern\_T\_camEye \quad \text{Eq 3:}$$

Since there may be N such calibration images and associated respective camera eye poses, there can be N occurrences of camTarget_T_camEye calculated. To reduce the effects of measurement noise and systemic error, the N occurrences of camTarget_T_camEye can be averaged to find a final camTarget_T_camEye for each camera eye.

In some embodiments calTarget_T_calPattern can be made by design to be the identity matrix, simplifying the equation.

The Tx, Ty, Tz translations are each averaged in a linear manner.

Averaging rotations Rx, Ry, Rz can be performed, for example, by converting the angular set to quaternions, checking that none are polar opposites and solving using, for example, a Markely-type method.

After the above steps are complete, system calibration may be deemed as complete.

In a typically offline process, the patient can be scanned volumetrically resulting in a three-dimensional sampling of the relevant patient anatomy in some reference frame (e.g., a reference frame of the scanning device).

The navigated target mounted to the patient clamp may also referred to as the "patient reference target." The patient reference target plays a similar role during runtime use of the system as the navigated target mounted to the calibration object did during the calibration process.

A patient registration process can be performed, resulting in knowledge of the pose of the relevant patient anatomy relative to the patient reference target and denoted as:

patientTarget_T_patientData (2.5)

Finding where the camera eyes are looking in the patient data

The combination of the information described above may be used to determine where each of the respective camera eyes of the stereoscopic digital surgical microscope are looking in the patient data during runtime use of the system. In modern computer graphics systems, the inverse of this construct can be calculated. Thus, the pose of the patient data in each of the respective camera eyes of the stereoscopic digital surgical microscope is determined as:

$$camEye\_T\_patientData = camEye\_T\_camTarget*camTarget\_T\_localizer*localizer\_T\_patientTarget*patientTarget\_T\_patientData \quad \text{Eq 4:}$$

The above described equation may be the "model-view" portion of setting up the computer graphics renderer; the equation describes how the model (e.g., the patient data) is to be viewed.

A projection matrix of the computer graphics system may be used to describe how points in the scene are projected onto the display screen. The camera calibration process may be similar to determining how points in the scene are projected onto the camera's image sensor. The camera intrinsics resulting from camera calibration may be used directly in creating the projection matrix.

In some computer graphics systems (e.g., OpenGL), the final projection process can also include a mapping to an interim space (e.g., the normalized device coordinate space). This can be achieved by taking the projection matrix just described and pre-multiplying by another matrix. The result can also be referred to as a projection matrix, and may offer the opportunity to directly manipulate the field of view as is described next. For simplicity, the result may be referred to as the combined projection matrix.

In association with the image sensor width and height ratio, the camera intrinsic parameters known as "focal length" may describe the angle of view of the camera and may be used directly in the projection matrix.

An optional explicit field of view calibration improves on this and may be used in some embodiments. The optional explicit field of view calibration may require an additional focus distance calibration as will be described herein.

A calibrated measurement tool such as a ruler with gradations may be placed in the scene such that its image may align with, and therefore measure, a relevant dimension of the screen (e.g., the horizontal width of the screen).

The camera may be set to some zoom and working distance setting. The ruler may be brought into focus by moving the camera head mechanically. The screen width (e.g., the horizontal field of view at the focal surface) may be read directly from the ruler.

The process may be repeated over multiple optical settings (e.g., six zooms and six working distances spanning each respective range for a total of thirty-six measurements). The results may fit to respective curves in a parameterization process as described herein, thus providing an accurate measure of the (in this example) horizontal field of view over the whole zoom and working distance range.

To assist in automating this process, a pattern may be used as the measurement tool. The pattern can be detected and measured by computer vision processes. For example, a flat plate can be adorned with a mostly symmetric checkerboard image. The dimensions of each feature of the checkerboard image may be known by design and/or measurement. Some asymmetry or other feature may be added to assist the computer vision processes as well as robot control such that the plate can be kept centered nominally in the camera view.

Multiple patterns of varying sizes may be optionally used to provide accurate calibration over a wide zoom range.

Traditional camera calibration can also provide a measure of the optical distortion of the system at the optical parameter settings at which the calibration process was performed. A set of distortion coefficients can be found and can be used in some embodiments to correct such optical distortion. In some embodiments, such distortion correction can be used to improve the field of view calibration method. Furthermore, in some embodiments, such distortion correction can be used to improve the accuracy of the overlay (e.g., how it matches the live view.)

In embodiments where an explicit field of view calibration process may be used to improve on the field of view determination for the projection matrix of the computer graphics renderer, the distance to the focal surface of each camera eye of the stereoscopic digital surgical microscope may be required to be calculated. The determination of this distance for each camera eye will be discussed herein, in relation to FIG. 21.

Figure 20:
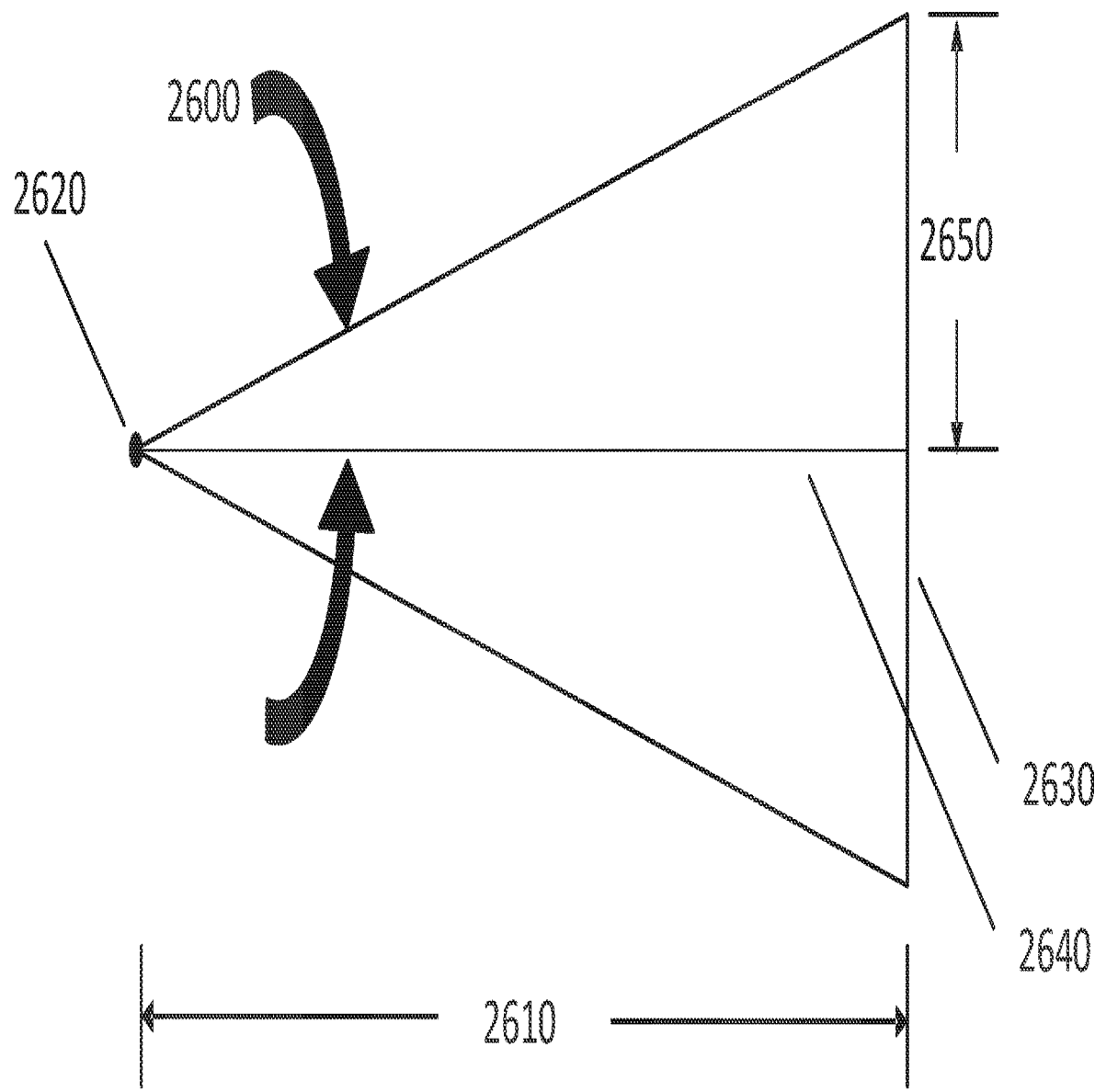
FIG. 20 is a diagram showing an angle of view applicable to the integrated surgical navigation and visualization system, according to an example embodiment of the present disclosure.

FIG. 20 is a diagram showing an angle of view applicable to the integrated surgical navigation and visualization system, according to an example embodiment of the present disclosure. With the focus distance, the angle of view can be calculated. This angle may be needed to calculate terms in the projection matrix and can be found by trigonometry, as shown in FIG. 20:

For example, the half angle 2600 can be found by measuring the focus distance 2610 from the camera center of projection (also referred to as the camera "eye point") 2620 to the focus surface 2630 along the optical axis 2640. The additional field of view calibration can provide a measure of the field of view (for example the horizontal width) at the focus surface. The half of such distance is shown as marker 2650. The tangent of half angle 2600 is distance 2650 divided by distance 2640. The inverse tangent function can then be used to calculate the "half field of view angle." The half field of view angle can be used to calculate directly certain matrix elements of the combined projection matrix as:

Matrix element (0,0)=1.0/tan(halfHorizontalFieldOfViewAngle), and
Matrix element (1,1)=1.0/tan(halfVerticalFieldOfViewAngle), where it should be noted that the horizontal and vertical field of view are related by the width and height ratio of the sensor (or equivalently of the images used in camera calibration.)

The previously described camEye_T_patientData in combination with the projection matrix utilizing camera intrinsics information determined earlier provide a faithful rendering of a duplicate representation from the (typically volumetric) patient data of any part of the relevant patient anatomy of the live patient that is within the field of view and depth of focus of the digital surgical microscope. Further, this rendering is effective in each respective eye of the digital surgical microscope, thereby enabling stereoscopic rendering of such a representation.

The rendering may be registered to the live patient view on the stereoscopic digital surgical microscope in the correct position, orientation and scale to within some tolerance of each. Further, the perspective of the render in three dimensions also matches the live view to within some tolerance.

These features along with appropriate user interface controls enable the user to "look inside" the patient even without making any incision. These features similarly allow the user to "look ahead" of where they currently are if for example they have made incisions and are performing a surgical approach to a pathology en route to providing therapy for said pathology.

Further, these features allow each of these capabilities to be viewed by the user in stereoscopic, which may greatly enhance spatial awareness and is more intuitive.

Further, these features allow the utilization of (typically volumetric) patient data on the same display as the live surgical site view, thereby reducing cognitive load of having to remember complex three-dimensional views when transitioning between the navigation device and the surgical visualization device. The presently described integrated surgical navigation and visualization system incorporates both devices, integrating them into a greater whole.

Figure 21:
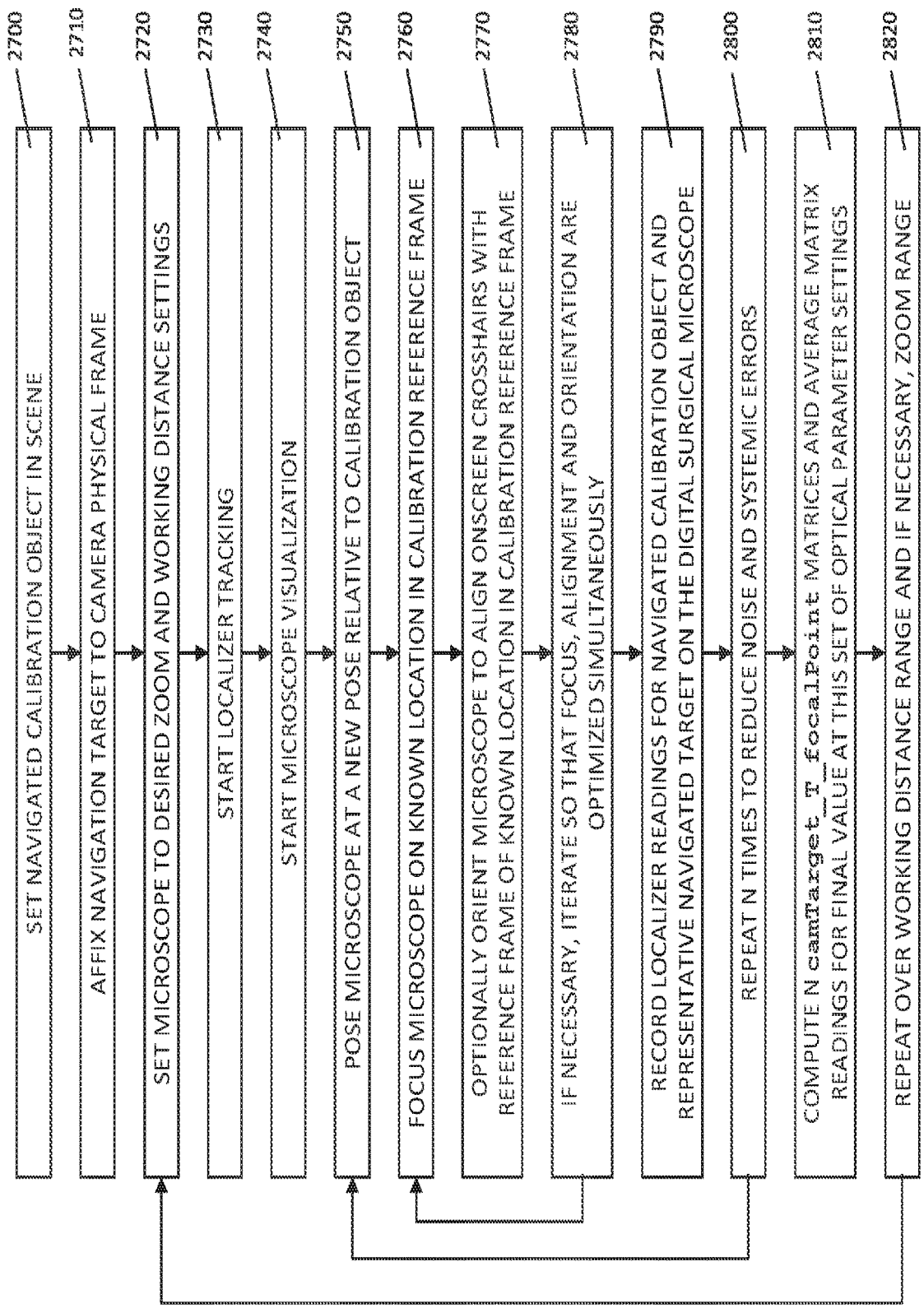
FIG. 21 is a flow diagram showing an example method for a focal reference frame calibration applicable to the integrated surgical navigation and visualization system, according to an example embodiment of the present disclosure.

FIG. 21 is a flow diagram showing an example method for a focal reference frame calibration applicable to the integrated surgical navigation and visualization system, according to an example embodiment of the present disclosure.

At step 2700, a navigated calibration object can be set into the scene. The calibration object may include one or more structures, (e.g., a crosshair) to aid alignment of the visually relevant reference frame of the microscope to the reference frame of the navigated calibration object (e.g., via a crosshair or other alignment aid on the navigated calibration object). Also or alternatively, the onscreen center and axes may be drawn onscreen by the graphics module to aid the operator in aligning the onscreen center to the calibration object alignment structure(s).

At step 2710, the navigation target may be affixed to the camera physical The microscope may be set to a desired zoom magnification and working distance settings at step 2720. The localizer tracking may be started at step 2730. The localizer may detect the presence of, and determine the pose in localizer space of, each trackable navigation target in its viewable scene. In some aspects, those targets may comprise the navigated calibration object and the representative navigated target on the digital surgical microscope.

At step 2740, microscope visualization can be started. At step 2750, the microscope can be posed relative to the navigated calibration target (or vice-versa.)

At 2760, the microscope can be focused on the calibration object alignment structure. For example, this structure may comprise a crosshair. To simplify and reduce error in the matrix calculations, the crosshair may be located at the origin of the calibration object's navigated target, and its X and Y axes may be coincident to those respectively of said target. The crosshair may be two-dimensional; the imagined Z axis may also taken to be coincident to the corresponding axis of the calibration object's navigated target.

At step 2770, the microscope may be optionally oriented to align the onscreen crosshairs with those of the calibration target. This step may be optional, for example, if the focal reference frame provides more information than is needed. In some embodiments, it may be sufficient to determine only the focal point location relative to the representative navigated target on the digital surgical microscope and to not also determine the orientation of the whole focal reference frame relative to said target.

Since changing the orientation of the microscope could change its optimal focus point, an iteration may be performed at step 2780 if appropriate to optimize the focus as well as the relative location (i.e. alignment) and orientation of the onscreen crosshairs to the calibration target crosshairs.

The localizer readings localizer_T_camTarget and localizer_T_calTarget may be recorded at step 2790. As noise reduction and systemic error reduction practices, it may be desirable to repeat, at step 2800, the overall measurement at a number (for example N=25) of different poses of the microscope relative to the navigated calibration target.

At step 2810, the function camTarget_T_focalRefFrame can be solved as:

$$\text{camTarget}\_T\_\text{focalRefFrame} = \text{camTarget}\_T\_\text{localizer} * \text{localizer}\_T\_\text{calTarget} * \text{calTarget}\_T\_\text{focalRefFrame},$$

where calTarget_T_focalRefFrame in some embodiments is identity by design to simplify and reduce errors in matrix multiplication. The simplified equation thus becomes:

$$\text{camTarget}\_T\_\text{focalRefFrame} = \text{camTarget}\_T\_\text{localizer} * \text{localizer}\_T\_\text{focalRefFrame}$$

These N solutions may be averaged using matrix averaging as described elsewhere in this document to determine a final value for camTarget_T_focalRefFrame.

For a more complete calibration, this process may be repeated at step 2820 at a number of zoom and working distance settings across the operating range of each such parameter. A curve may be fit for each relevant output parameter set as a function of input parameters. This process may be referred to as parameterization. The output parameter set may be the focal point pose relative to the representative navigated target on the digital surgical microscope. The input parameters may include zoom and working distance settings from the camera control module.

Using the previously described camTarget_T_camEye and camTarget_T_focalRefFrame functions, the focal point reference frame pose relative to each respective camera eye of the stereoscopic digital surgical microscope can be determined by:

$$\text{camEye}\_T\_\text{focalRefFrame} = \text{camEye}\_T\_\text{camTarget} * \text{camTarget}\_T\_\text{localizer} * \text{localizer}\_T\_\text{calTarget} * \text{calTarget}\_T\_\text{cal} \text{CoordSys} * \text{calCoordSys}\_T\_\text{focalRefFrame},$$

where calTarget_T_calCoordSys can allow for a transformation between the navigated target of the calibration object and an arbitrary coordinate system, and calCoordSys_T_focalRefFrame can allow for a transformation between that coordinate system and the focal reference frame. Both of these matrices may be identity matrices by design. The equation can thus be simplified as:

$$\text{camEye}\_T\_\text{focalRefFrame} = \text{camEye}\_T\_\text{camTarget} * \text{camTarget}\_T\_\text{localizer} * \text{localizer}\_T\_\text{focalRefFrame}.$$

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A surgical navigation system for patient registration comprising:
   a moveable arm;
   a visualization camera connected to the moveable arm, the visualization camera including at least one navigation camera trackable target mounted to a housing of the visualization camera;
   a navigation camera; and
   a computer system communicatively coupled to the visualization camera and the navigation camera, the computer system configured to:
   receive images of patient anatomy;
   solve for one or more camera parameters and one or more correction coefficients;
   for each received image,
      store, in a localizer space, a pose of the at least one navigation camera trackable target and a patient target, respectively as a Localizer_T_Camera-Target$_i$ transform and a Patient-Target_T_Localizer$_i$ transform;
      extract a model of the patient anatomy described in a photogrammetry reference frame using a photogrammetry module;
      solve for a camera optical reference frame pose relative to a photogrammetry reference frame to store as a Photogrammetry_T_Camera-Optical$_i$ transform;
      detect a target within the received image and use said target to set a scale;
      match the extracted model of the patient anatomy with a patient anatomy representation in patient data to obtain a Photogrammetry_T_Patient Data transform; and
      calculate, for each of the respective poses associated with the received image, a Patient-Target_T_Patient_Data$_i$ transform using the Patient-Target_T_Localizer$_i$ transform, the Localizer_T_Camera-Target$_i$ transform, a Camera-Target_T_Camera-Optical transform, the Photogrammetry_T_Camera-Optical$_i$ transform, and the Photogrammetry_T_Patient Data transform;
   average some or all of the Patient-Target_T_Patient_data$_i$ transforms of each of the respective poses associated with each of the received images to determine a single Patient-Target_T_Patient_Data transformation; and
   display, using the Patient-Target_T_Patient_Data$_i$ transformation, the patient data overlaid on live surgical images recorded by the visualization camera.

2. The system of claim 1, wherein the one or more camera parameters includes one or more of a focal length at one or more magnifications, a working distance to a target surgical site, an interpupillary distance between image sensors of the visualization camera, or a zoom repeat point, and
   wherein the one or more camera parameters includes information for modeling one or more of the image sensors of the visualization camera as respective pinhole cameras.

3. The system of claim 1, wherein the visualization camera comprises a stereoscopic camera.

4. The system of claim 1, wherein the patient data includes at least one of preoperative images, CT images, MRI images, a three-dimensional model of the patient anatomy, surgical templates, or surgical planning markers.

5. The system of claim 1, wherein a transform between a reference frame of a computer vision readable target and the at least one navigation camera trackable target is known by design, or determined by measurement.

6. The system of claim 1, wherein the visualization camera is used as the navigation camera such that the Camera-Target_T_Camera-Optical transform and the Localizer_T_Camera-Target$_i$ transform are not needed.

7. The system of claim 1, wherein the computer system is further configured to:
 identify features within some or all of the received images; and
 match the features across some or all the received images.

8. The system of claim 1, wherein the extracted model of the patient anatomy is matched with the patient anatomy representation via user guidance or automatic alignment.

9. A system for determining a pose of a camera optical reference frame relative to a camera navigation target, the system comprising:
 a processor; and
 a memory storing instructions that, when executed by the processor, cause the processor to:
  receive, via a visualization camera, images of a navigated calibration device,
  solve for camera parameters and correction coefficients,
  for each received image,
   store, in a localizer space, a pose of the camera navigation target and a calibration device navigation target, respectively as a Localizer_T_Camera-Target$_i$ transform and a Localizer_T_Calibration-Device$_i$ transform,
   extract a model of a scene provided in a reference frame as selected by a photogrammetry module,
   solve for a camera optical reference frame pose relative to a photogrammetry reference frame to store as a Photogrammetry_T_Camera-Optical$_i$ transform,
   detect a computer vision readable target on the navigated calibration device and convert to a reference frame,
   use the computer vision readable target to set a scale,
   store a pose of the reference frame of the computer vision readable target in the photogrammetry reference frame as a Photogrammetry_T_CV-Readable-Target transform,
   calculate a Calibration-Device_T_CV-Readable-Target transform between the reference frame of the computer vision readable target and the calibration device navigation target,
   generate, using the Calibration-Device_T_CV-Readable-Target transform, the Photogrammetry_T_CV-Readable-Target transform, and the Photogrammetry_T_Camera-Optical$_i$ transform, a camera optical reference frame pose relative to the calibration device navigation target as a Calibration-Device_T_Camera-Optical$_i$ transform, and
   generate, using the stored poses in the localizer space of the camera navigation target and the calibration device navigation target, respective camera optical reference frame poses relative to the camera navigation target such that a Camera-Target_T_Camera-Optical$_i$ transform is equal to a combination of the Localizer_T_Camera-Target$_i$ transform, the Localizer_T_Calibration-Device$_i$ transform, and the Calibration-Device_T_Camera-Optical$_i$ transform, and
  determine, as a Camera-Target_T_Camera-Optical transform, a single camera optical reference frame pose relative to the camera navigation target by averaging results of the same for all received images.

10. The system of claim 9, wherein the camera parameters include one or more of:
 a focal length at one or more magnifications;
 a working distance to the camera navigation target;
 an interpupillary distance between image sensors of the visualization camera; or
 a zoom repeat point, and
 wherein the camera parameters include information for modeling one or more of the image sensors of the visualization camera as respective pinhole cameras.

11. The system of claim 9, wherein the visualization camera comprises a stereoscopic camera.

12. The system of claim 9, wherein the transform between the reference frame of the computer vision readable target and the calibration device navigation target is known by design, or determined by measurement.

13. The system of claim 9, wherein the visualization camera is used as a navigation camera.

14. The system of claim 9, wherein the instructions, when executed, further cause the processor to:
 identify features within the received images; and
 match the features across the received images.

15. A method for patient registration in a surgical navigation system, the method comprising:
 receiving, by a computer system communicatively coupled to a visualization camera and a navigation camera, images of patient anatomy;
 solving for one or more camera parameters and one or more correction coefficients;
 for each received image:
  storing, in a localizer space, a pose of a navigation camera trackable target and a patient target, respectively as a Localizer_T_Camera-Target$_i$ transform and a Patient-Target_T_Localizer$_i$ transform;
  extracting a model of a patient anatomy described in a photogrammetry reference frame using a photogrammetry module;
  solving for a camera optical reference frame pose relative to a photogrammetry reference frame to store as a Photogrammetry_T_Camera-Optical$_i$ transform;
  detecting a target within the received image and use said target to set a scale;
  matching the extracted model of the patient anatomy with a patient anatomy representation in patient data to obtain a Photogrammetry_T_Patient Data transform; and
  calculating, for each of the respective poses associated with the received image, a Patient-Target_T_Patient_Data$_i$ transform using the Patient-Target_T_Localizer$_i$ transform, the Localizer_T_Camera-Target$_i$ transform, a Camera-Target_T_Camera-Optical transform, the Photogrammetry_T_Camera-Optical$_i$ transform, and the Photogrammetry_T_Patient Data transform;
 averaging some or all of the Patient-Target_T_Patient_data$_i$ transforms of each of the respective poses associated with each of the received images to determine a single Patient-Target_T_Patient_Data transformation; and displaying, using the Patient-Target_T_Patient_Data transformation, the patient data overlaid on live surgical images recorded by the visualization camera.

16. The method of claim 15, wherein the one or more camera parameters includes one or more of:
a focal length at one or more magnifications;
a working distance to a target surgical site;
an interpupillary distance between left and right image sensors of the visualization camera; or
a zoom repeat point,
wherein the one or more camera parameters includes information for modeling the left and right image sensors of the visualization camera as respective pinhole cameras.

17. The method of claim 15, wherein the patient data includes at least one of preoperative images, CT images, MRI images, a three-dimensional model of the patient anatomy, surgical templates, or surgical planning markers.

18. The method of claim 15, wherein a transform between a reference frame of a computer vision readable target and the navigation camera trackable target is known by design, or determined by measurement.

19. The method of claim 15, further comprising:
identifying features within some or all of the received images; and
matching the features across some or all the received images.

20. The method of claim 15, wherein the extracted model of the patient anatomy is matched with the patient anatomy representation via user guidance or automatic alignment.

* * * * *